(12) United States Patent
Arimori et al.

(10) Patent No.: US 7,943,614 B2
(45) Date of Patent: *May 17, 2011

(54) CARBOXAMIDE COMPOUND AND USE OF THE SAME

(75) Inventors: Sadayuki Arimori, Toyonaka (JP); Yoshiharu Kinoshita, Misawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 642 days.

This patent is subject to a terminal disclaimer.

(21) Appl. No.: 11/988,662

(22) PCT Filed: Jul. 12, 2006

(86) PCT No.: PCT/JP2006/314204
§ 371 (c)(1), (2), (4) Date: Mar. 11, 2008

(87) PCT Pub. No.: WO2007/007905
PCT Pub. Date: Jan. 18, 2007

(65) Prior Publication Data
US 2009/0111815 A1    Apr. 30, 2009

(30) Foreign Application Priority Data

Jul. 14, 2005 (JP) ................. 2005-205248
Nov. 28, 2005 (JP) ................. 2005-341612
Apr. 25, 2006 (JP) ................. 2006-120175

(51) Int. Cl.
*A01N 43/60* (2006.01)
*A01N 43/58* (2006.01)
*C07D 401/12* (2006.01)
*C07D 207/36* (2006.01)

(52) U.S. Cl. ............... 514/242; 514/245; 514/252.02; 514/255.02; 514/275; 514/299; 544/182; 544/197; 544/405; 546/183

(58) Field of Classification Search ............... None
See application file for complete search history.

(56) References Cited

U.S. PATENT DOCUMENTS

| 4,578,394 A | 3/1986 | Allen et al. |
| 4,966,908 A | 10/1990 | Eckhardt et al. |
| 5,330,995 A | 7/1994 | Eicken et al. |
| 2004/0204470 A1 | 10/2004 | Elbe et al. |
| 2008/0058389 A1 | 3/2008 | Dunkel et al. |

FOREIGN PATENT DOCUMENTS

| EP | 0 334 809 A2 | 9/1989 |
| WO | WO-02/38542 A1 | 5/2002 |
| WO | WO-2006/129432 A1 | 12/2006 |
| WO | WO-2007/007903 A2 | 1/2007 |

*Primary Examiner* — Zinna N Davis
(74) *Attorney, Agent, or Firm* — Birch, Stewart, Kolasch & Birch, LLP

(57) ABSTRACT

A carboxamide compound represented by the formula (I):

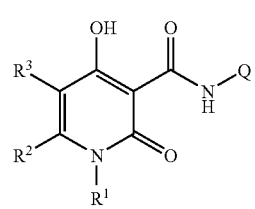

[wherein Q represents a nitrogen-containing 6-membered aromatic heterocyclic group optionally fused with a benzene ring, two or more ring constitutional atoms of the heterocyclic group are a nitrogen atom, and the heterocyclic group may be substituted with at least one group selected from the group consisting of a C1-C3 alkyl group etc.], and a plant disease controlling agent comprising this as an active ingredient.

12 Claims, No Drawings

CARBOXAMIDE COMPOUND AND USE OF THE SAME

This application is a 371 of PCT/JP2006/314204 filed Jul. 12, 2006.

TECHNICAL FIELD

The present invention relates to a carboxamide compound, and use of the same.

BACKGROUND ART

Development of a plant disease controlling agent has been progressed, and compounds having controlling activity on many plant diseases have been found out.

However, plant disease controlling activity of these compounds is not sufficient in some cases.

DISCLOSURE OF THE INVENTION

An object of the present invention is to provide a compound having excellent plant disease controlling activity.
The present invention is as follows:

[1] A carboxamide compound (hereinafter, referred to as present compound) represented by the formula (I):

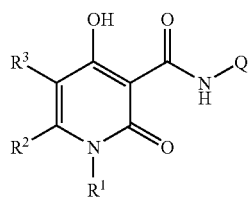

(I)

[wherein Q represents a nitrogen-containing 6-membered aromatic heterocyclic group optionally fused with a benzene ring, two or more of ring constitutional atoms of the heterocyclic group are nitrogen atoms, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group,
$R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end to represent a C3-C4 alkylene group, and
$R^3$ represents a hydrogen atom, a halogen atom or a C1-C3 alkyl group].

[2] The carboxamide compound according to [1], wherein Q represents a nitrogen-containing 6-membered aromatic heterocyclic group optionally fused with a benzene ring, two or more of ring constitutional atoms of the heterocyclic group are nitrogen atoms, the heterocyclic group may be substituted with at least one group selected from of the group consisting of a C1-C3 alkyl group, a C1-C3 haloalkyl group, a C1-C3 alkoxy group, a halogen atom, a cyano group and a nitro group,
$R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end, to represent a C3-C4 alkylene group, and
$R^3$ represents a hydrogen atom, a halogen atom or a C1-C3 alkyl group.

[3] The carboxamide compound according to [1], wherein Q is a 6-membered aromatic heterocyclic group in which two or more of ring constitutional atoms are nitrogen atoms, and the heterocyclic group may be substituted with at least one group selected from the group consisting of a C1-C3 alkyl group, C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group.

[4] The carboxamide compound according to [1], wherein Q is a 6-membered aromatic heterocyclic group in which two or more of ring constitutional atoms are nitrogen atoms, and the heterocyclic group may be substituted with at least one group selected from the group constituting of a C1-C3 alkyl group, a C1-C3 haloalkyl group, a C1-C3 alkoxy group, a halogen atom, a cyano group and a nitro group.

[5] The carboxamide compound according to [1], wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl) C1-C3 alkylthio group, a halogen atom, a cyano group and a nitro group.

[6] The carboxamide compound according to [1], wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group.

[7] The carboxamide compound according to [1], wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group.

[8] The carboxamide compound according to [1], wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group and a 1,3,5-triazin-2-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group.

[9] The carboxamide compound according to any one of [1] to [8], wherein $R^3$ is a hydrogen atom or a C1-C3 alkyl group.

[10] The carboxamide compound according to any one of [1] to [8], wherein $R^3$ is a hydrogen atom or a halogen atom.

[11] A plant disease controlling agent, comprising a carboxamide compound as defined in any one of [1] to [10] as an active ingredient, and an inert carrier.

[12] A method of controlling a plant disease, comprising a step of treating a plant or a soil where a plant grows with an effective amount of the carboxamide compound as defined in any one of [1] to [10].

[13] Use of a carboxamide compound as defined in any one of [1] to [10] for controlling a plant disease.

Examples of the C1-C3 alkyl group represented by $R^1$ include a methyl group, an ethyl group, a propyl group and an isopropyl group, and examples of the C2-C5 alkoxyalkyl group include a methoxymethyl group, an ethoxymethyl group, and a propoxymethyl group.

Examples of the C1-C3 alkyl group represented by $R^2$ include a methyl group, an ethyl group, a propyl group and an isopropyl group.

Examples of the C3-C4 alkylene group in which $R^1$ and $R^2$ are bound to each other at an end include a trimethylene group and a tetramethylene group.

Examples of the halogen atom represented by $R^3$ include a fluorine atom, a chlorine atom, a bromine atom and an iodine atom.

Examples of the C1-C3 alkyl group represented by $R^3$ include a methyl group, an ethyl group, a propyl group, and an isopropyl group.

Q represents a nitrogen-containing 6-membered aromatic heterocyclic group optionally fused with a benzene ring, two or more of ring constitutional atoms of the heterocyclic group are nitrogen atoms, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group.

Examples of such the heterocyclic group include a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinazolin-2-yl group in which a pyrimidine ring is fused with a benzene ring, a quinoxalin-2-yl group in which a pyrazinyl ring is fused with a benzene ring, a cinnolin-3-yl group in which a pyridazine ring is fused with a benzene ring, and groups in which these heterocyclic groups are substituted with at least one group selected from the group consisting of a C1-C3 alkyl group (e.g. methyl group, ethyl group, propyl group etc.), a C1-C3 haloalkyl group (e.g. trifluoromethyl group, etc.), a C1-C3 alkoxy group (e.g. methoxy group, ethoxy group etc.), a C1-C3 alkylthio group (e.g. methylthio group, ethylthio group and propylthio group), a (C1-C3 alkoxycarbonyl)C1-C3 alkylthio group (e.g. methoxycarbonylmethylthio group, ethoxycarbonylmethylthio group and 1-(methoxycarbonyl)ethylthio group), a halogen atom (e.g. fluorine atom, chlorine atom etc.), a cyano group and a nitro group.

Specific examples of the heterocyclic group represented by Q include:

a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a 5-chloro-2-pyrimidinyl group, a 2-chloro-5-pyrimidinyl group, a 5-chloro-2-pyrazinyl group, a 6-chloro-3-pyridazinyl group, a 5-methyl-2-pyrimidinyl group, a 2-methyl-5-pyrimidinyl group, a 5-methyl-2-pyrazinyl group, a 6-methyl-3-pyridazinyl group, a 5-trifluoromethyl-2-pyrimidinyl group, a 2-methoxy-5-pyrimidinyl group, a 5-cyano-2-pyrazinyl group, a 6-nitro-3-pyridazinyl group, a quinoxalin-2-yl group, a quinazolin-2-yl group, a cinnolin-3-yl group, a 6-chloro-2-pyrazinyl group, a 6-methoxy-4-pyrimidinyl group, a 4-methyl-2-pyrimidinyl group, a 6-methoxy-3-pyridazinyl group, a 6-bromo-3-pyridazinyl group, a 6-cyano-3-pyridazinyl group, a 6-methylthio-3-pyridazinyl group, a 6-methoxycarbonylmethylthio-3-pyridazinyl group, a 5-bromo-2-pyrimidinyl group, a 6-ethyl-3-pyridazinyl group, a 6-propyl-3-pyridazinyl group, a 2-ethoxy-5-pyrimidinyl group, a 6-ethoxy-3-pyridazinyl group, a 6-ethylthio-3-pyridazinyl group, a 6-ethoxycarbonylmethylthio-3-pyridazinyl group, a 5-fluoro-2-pyrimidinyl group, a 2-fluoro-5-pyrimidinyl group, a 5-fluoro-2-pyrazinyl group, a 6-fluoro-3-pyridazinyl group, a 2-bromo-5-pyrimidinyl group, a 5-bromo-2-pyrazinyl group, a 5-cyano-2-pyrimidinyl group and a 2-cyano-5-pyrimidinyl group.

Examples of embodiments of the present compound include the following carboxamide compounds in the present compounds.

A carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a 6-membered aromatic heterocyclic group having two or more nitrogen atoms as ring constitutional atoms, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a 6-membered aromatic heterocyclic group having two or more nitrogen atoms as ring constitutional atoms, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group, and $R^3$ is a hydrogen atom or a C1-C3 alkyl group in the formula (I);

a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group, and $R^3$ is a hydrogen atom or a C1-C3 alkyl group in the formula (I);

a carboxamide compound in which Q is a heterocyclic group which is a pyrimidinyl group, a pyrazinyl group, a pyridazinyl group, a 1,2,4-triazinyl group or a 1,3,5-triazinyl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a heterocyclic group which is a pyrimidinyl group, a pyrazinyl group and a pyridazinyl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group in the formula (I);

a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which Q is a 6-membered aromatic heterocyclic group having two or more nitrogen atoms as ring constitutional atoms, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which $R^3$ is a hydrogen atom or a C1-C3 alkyl group in the formula (I);

a carboxamide compound in which Q is a 6-membered aromatic heterocyclic group having two or more nitrogen atoms as ring constitutional atoms, the heterocyclic group may be substituted with at least one group selected from the group consisting of a C1-C3 alkyl group, a C1-C3 haloalkyl group, a C1-C3 alkoxy group, a halogen atom, a cyano group and a nitro group, and $R^3$ is a hydrogen atom or a C1-C3 alkyl group in the formula (I);

a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a halogen atom, a cyano group and a nitro group, and $R^3$ is a hydrogen atom or a C1-C3 alkyl group in the formula (I);

a carboxamide compound in which Q is a heterocyclic group which is a pyrimidinyl group, a pyrazinyl group, a pyridazinyl group, a 1,2,4-triazinyl group or a 1,3,5-triazinyl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which Q is a heterocyclic group which is a pyrimidinyl group, a pyrazinyl group or a pyridazinyl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group in the formula (I);

a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, and the heterocyclic group may be substituted with at least one group selected from the group consisting of a methyl group, a methoxy group, a methylthio group, a methoxycarbonylmethylthio group, a bromine atom, a chlorine atom and a cyano group in the formula (I);

a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, and the heterocyclic group may be substituted with at least one group selected from the group consisting of a methyl group, a methoxy group, a chlorine atom, and a cyano group in the formula (I);

a carboxamide compound in which $R^2$ is a hydrogen atom, and $R^3$ is a hydrogen atom in the formula (I);

a carboxamide compound in which $R^2$ is a methyl group, and $R^3$ is a hydrogen atom in the formula (I);

a carboxamide compound in which $R^2$ is a hydrogen atom, and $R^3$ is a methyl group in the formula (I);

a carboxamide compound in which $R^1$ is a methyl group, $R^2$ is a hydrogen atom, and $R^3$ is a hydrogen atom in the formula (I);

a carboxamide compound in which $R^1$ is a methyl group, $R^2$ is a methyl group, and $R^3$ is a hydrogen atom in the formula (I);

a carboxamide compound in which $R^1$ is a methyl group $R^2$ is a hydrogen atom, and $R^3$ is a methyl group in the formula (I);

a carboxamide compound in which $R^2$ is a hydrogen atom, and $R^3$ is a fluorine atom in the formula (I);

a carboxamide compound in which $R^2$ is a methyl group, and $R^3$ is a fluorine atom in the formula (I);

a carboxamide compound in which $R^2$ is a hydrogen atom, and $R^3$ is a chlorine atom in the formula (I);

a carboxamide compound in which $R^2$ is a methyl group, and $R^3$ is a chlorine atom in the formula (I);

a carboxamide compound in which $R^1$ is a methyl group, $R^2$ is a hydrogen atom, and $R^3$ is a fluorine atom in the formula (I);
a carboxamide compound in which $R^1$ is a methyl group, $R^2$ is a methyl group, and $R^3$ is a fluorine atom in the formula (I);
a carboxamide compound in which $R^1$ is a methyl group, $R^2$ is a hydrogen atom, and $R^3$ is a chlorine atom in the formula (I);
a carboxamide compound in which $R^1$ is a methyl group, $R^2$ is a methyl group, and $R^3$ is a chlorine atom in the formula (I);
a carboxamide compound in which $R^1$ and $R^2$ are bound to each other at an end to be a trimethylene group, and $R^3$ is a hydrogen atom in the formula (I);
a carboxamide compound in which $R^1$ and $R^2$ are bound to each other at an end to be a trimethylene group, and $R^3$ is a fluorine atom in the formula (I);
a carboxamide compound in which $R^1$ and $R^2$ are bound to each other at an end to be a trimethylene group, and $R^3$ is a chlorine atom in the formula (I);
a carboxamide compound in which Q is a heterocyclic group which is a pyrimidinyl group, a pyrazinyl group, a pyridazinyl group, a 1,2,4-triazinyl group or a 1,3,5-triaziyl group, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3alkylthio group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group, and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a pyrimidinyl group, a pyrazinyl group or a pyridazinyl group, the heterocyclic group may be substituted with at least one group selected from the group consisting of a C1-C3 alkyl group, a C1-C3 haloalkoxy group, a C1-C3 alkoxy group, a C1-C3 alkylthio group, a (C1-C3 alkoxycarbonyl) C1-C3 alkylthio group, a halogen atom, a cyano group, and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl) C1-C3 alkylthio group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a pyrimidinyl group, a pyrazinyl group, a pyridazinyl group, a 1,2,4-triazinyl group or a 1,3,5-triazinyl group, the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a pyrimidinyl group, a pyrazinyl group or a pyridazinyl group, the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, the heterocyclic group may be substituted with at least one group selected from the group consisting of a methyl group, a methoxy group, a methylthio group, a methoxycarbonylmethylthio group, a bromine atom, a chlorine atom and a cyano group, $R^1$ is a C1-C3 alkyl group, $R^2$ is a hydrogen atom or a C1-C3 alkyl group, and $R^3$ is a hydrogen atom or a C1-C3 alkyl group in the formula (I);
a carboxamide compound in which Q is a heterocyclic group which is a 2-pyrimidinyl group, a 4-pyrimidinyl group, a 2-pyrazinyl group, a 3-pyridazinyl group, a 1,2,4-triazin-3-yl group or a 1,3,5-triazin-2-yl group, the heterocyclic group may be substituted with at least one group selected from the group consisting of a methyl group, a methoxy group, a chlorine atom and a cyano group, $R^1$ is a C1-C3 alkyl group, $R^2$ is a hydrogen atom or a C1-C3 alkyl group, and $R^3$ is a hydrogen atom or a C1-C3 alkyl group in the formula (I);

a carboxamide compound represented by the formula (I-100):

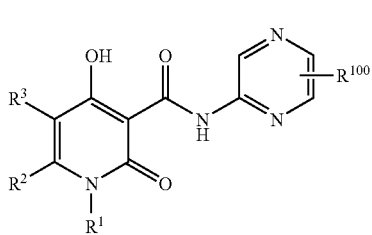

(I-100)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{100}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{100}$ is a hydrogen atom, a C1-C3 alkyl group, a C1-C3 haloalkyl group, a C1-C3 alkoxy group, a halogen atom, a cyano group or a nitro group in the formula (I-100);

a carboxamide compound represented by the formula (I-101):

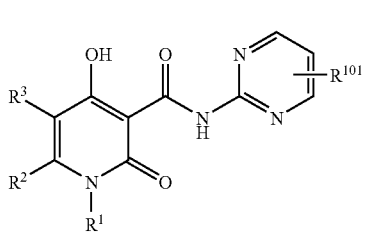

(I-101)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{101}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{101}$ is a hydrogen atom, a C1-C3 alkyl group, a C1-C3 haloalkyl group, a C1-C3 alkoxy group, a halogen atom, a cyano group or a nitro group in the formula (I-101);

a carboxamide compound represented by the formula (I-102):

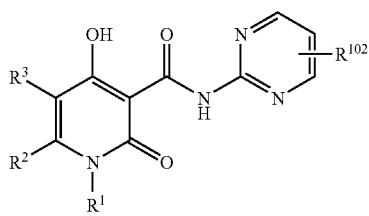

(I-102)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{102}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{102}$ is a hydrogen atom, a C1-C3 alkyl group, a C1-C3 haloalkyl group, a C1-C3 alkoxy group, a halogen atom, a cyano group or a nitro group in the formula (I-102);

a carboxamide compound represented by the formula (I-103):

(I-103)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{103}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{103}$ is a hydrogen atom, a C1-C3 alkyl group, a C1-C3 haloalkyl group, a C1-C3 alkoxy group, a halogen atom, a cyano group or a nitro group in the formula (I-103);

a carboxamide compound represented by the formula (I-104):

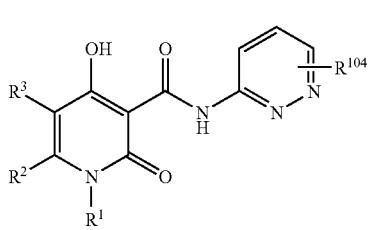
(I-104)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{104}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{104}$ is a hydrogen atom, a C1-C3 alkyl group, a C1-C3 haloalkyl group, a C1-C3 alkoxy group, a halogen atom, a cyano group or a nitro group in the formula (I-104);

a carboxamide compound represented by the formula (I-105):

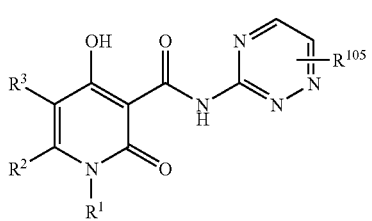
(I-105)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{105}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group,
and
$R^{105}$ is a hydrogen atom, a C1-C3 alkyl group, a C1-C3 haloalkyl group, a C1-C3 alkoxy group, a halogen atom, a cyano group or a nitro group in the formula (I-105);

a carboxamide compound represented by the formula (I-106):

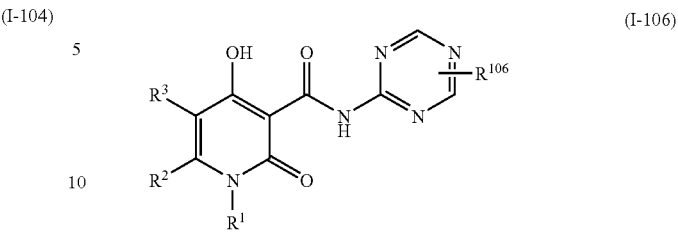
(I-106)

in which $R^1$ represents a C1-C3 alkyl group or a C2-C5 alkoxyalkyl group,
$R^2$ represents a hydrogen atom or a C1-C3 alkyl group,
$R^3$ represents a hydrogen atom, a halogen atom or a C1-C3 alkyl group,
$R^{106}$ represents a hydrogen atom, a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group or a nitro group;
a carboxamide compound in which $R^1$ is a C1-C3 alkyl group or a C2-C5 alkoxyalkyl group,
$R^2$ is a hydrogen atom or a C1-C3 alkyl group,
$R^3$ is a hydrogen atom, a halogen atom or a C1-C3 alkyl group, and
$R^{106}$ is a hydrogen atom, a C1-C3 alkyl group, a C1-C3 haloalkyl group, a C1-C3 alkoxy group, a halogen atom, a cyano group or a nitro group in the formula (I-106), Next, a process for preparing the present compound will be explained. The present compound can be prepared, for example, according to the following (Process A), (Process B) and (Process C).

In the (Process A), (Process B), (Process C), and Reference Process, if necessary, a protecting group for protecting a particular functional group may be used, and the protecting group can be deprotected under the suitable condition.

(Process A)

The present compound can be prepared by reacting a compound represented by the formula (II) and a compound represented by the formula (III).

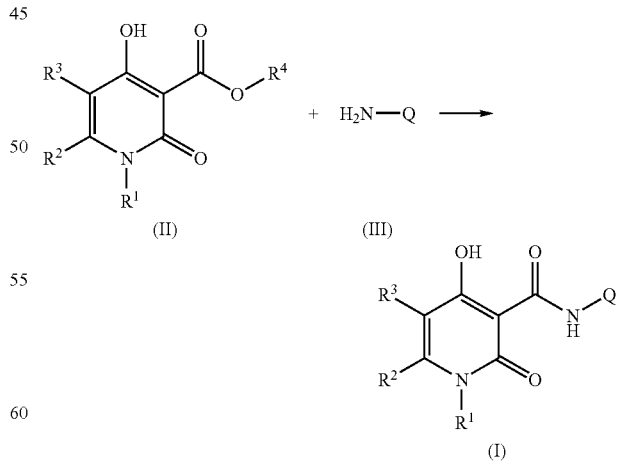

[wherein Q represents a nitrogen-containing 6-membered aromatic heterocyclic group optionally fused with a benzene ring, two or more of ring constitutional atoms of the heterocyclic group are nitrogen atoms, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl) C1-C3 alkylthio group, a halogen atom, a cyano group and a nitro group, $R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end, to represent a C3-C4 alkylene group, $R^3$ represents a hydrogen atom, a halogen atom or a C1-C3 alkyl group, and $R^4$ represents a C1-C10 alkyl group]

The reaction is performed usually in the presence of a solvent. If necessary, the reaction may be performed while a C1-C10 alcohol produced accompanying with progression of the reaction is removed by adsorbsion, distillation, or azeotropy or the like.

Examples of the solvent to be used in the reaction include halogenated aromatic hydrocarbons such as chlorobenzene, bromobenzene and the like, aromatic hydrocarbons such as toluene, xylene, and the like, acid amides such as N,N-dimethylformamide and the like, and a mixture thereof.

At the reaction, the compound represented by the formula (II) is usually used at a ratio of 0.1 to 5 moles per 1 mole of the compound represented by the formula (III).

A reaction temperature in the reaction is usually in a range of 80 to 180° C., and a reaction time is usually in a range of 0.1 to 24 hours. After completion of the reaction, the present compound represented by the formula (I) can be isolated, for example, by performing the following post-treatment procedure.

The reaction mixture is cooled to room temperature, the resultant solid is collected by filtration, and the solid is washed with an organic solvent, and dried; the reaction mixture is concentrated under reduced pressure, and the resulting solid is further washed with an organic solvent, and dried.

The isolated present compound represented by the formula (I) may be further purified by a procedure such as chromatography, recrystallization and the like.

(Process B)

The present compound can be prepared by reacting a compound represented by the formula (XIII) and a compound represented by the formula (III) using carbonyldiimidazole.

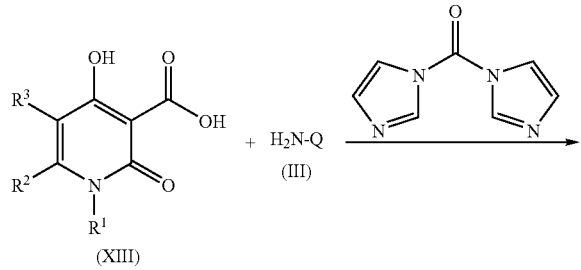

[wherein $R^1$, $R^2$, $R^3$ and Q are as defined above.]

The reaction is performed usually in the presence of a solvent. Examples of the solvent to be used in the reaction include nitriles such as acetonitrile, propionitrile and the like, ethers such as diethyl ether, t-butyl methyl ether, tetrahydrofuran, 1,4-dioxane and the like, aromatic hydrocarbons such as toluene, xylene, and the like, acid amides such as N,N-dimethylformamide and the like, and a mixture thereof.

At the reaction, the compound represented by the formula (III) is used usually at a ratio of 0.1 to 5 moles per 1 mole of the compound represented by the formula (XIII). Carbonyldiimidazole is used usually at a ratio of 0.1 to 5 moles per 1 mole of the compound represented by the formula (XIII).

A reaction temperature in the reaction is usually in a range of −10 to 150° C. and a reaction time is usually in a range of 0.1 to 24 hours.

After completion of the reaction, the present compound represented by the formula (I) can be isolated by performing a post-treatment procedure such as the resulting solid being collected by filtration, washing the solid with an organic solvent, drying and so on. The isolated present compound represented by the formula (I) may be further purified by a procedure such as chromatography, recrystallization and the like.

(Process C)

The present compound can be prepared by reacting a compound represented by the formula (XIII) and a compound represented by the formula (XV) in the presence of alkaline earth metal triflate such as magnesium triflate, calcium triflate and the like.

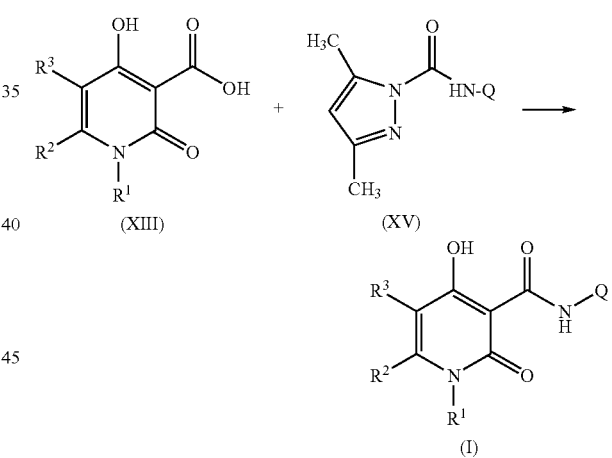

[wherein $R^1$, $R^2$, $R^3$ and Q are as defined above]

The reaction is performed usually in the presence of a solvent. Examples of the solvent used in the reaction include aromatic hydrocarbons such as toluene, xylene and the like.

At the reaction, the compound represented by the formula (XV) is usually used at a ratio of 1 mole per 1 mole of the compound represented by the formula (XIII), and the alkaline earth metal triflate is usually used at a ratio of 0.01 to 0.1 mole per 1 mole of the compound represented by the formula (XIII).

A reaction temperature in the reaction is usually in a range of 100 to 150° C. and a reaction time is usually in a range of 0.1 to 24 hours.

After completion of the reaction, the present compound represented by the formula (I) can be isolated by performing a post-treatment procedure such as the reaction mixture being cooled, the resulting solid being collected by filtration, washing the solid with an organic solvent, drying and so on. The isolated compound represented by the formula (I) may be further purified by a procedure such as chromatography, recrystallization and the like. The compound represented by the formula (XV) can be prepared from a compound represented by the formula (XVI):

OCN-Q (XVI)

and 3,5-dimethylimidazole.

Next, a process for preparing an intermediate for preparing the present compound will be explained as Reference Process.

(Reference Process 1)

A compound represented by the formula (II-1) among the compounds represented by the formula (II) can be prepared, for example, from a compound represented by the formula (IV) according to the following scheme.

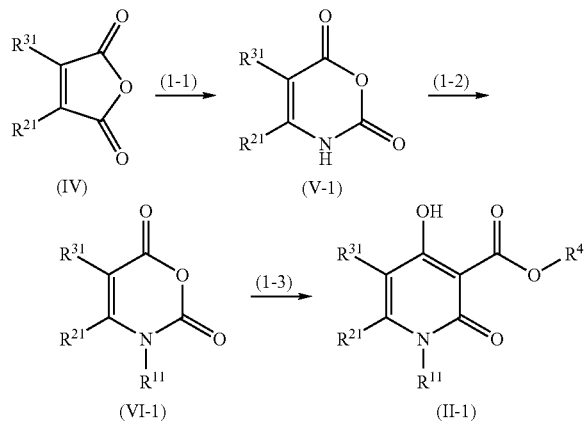

[wherein Q is as defined, $R^{11}$ represents a C1-C3 alkyl group or a C2-C5 alkoxyalkyl group, $R^{21}$ represents a hydrogen atom or a C1-C3 alkyl group, $R^{31}$ represents a hydrogen atom or a C1-C3 alkyl group, and $R^4$ represents a C1-C10 alkyl group]

Step (1-1)

A compound represented by the formula (V-1) can be prepared by reacting a compound represented by the formula (IV) with an azide compound (e.g. sodium azide, and trimethylsilyl azide), and further reacting the resulting product and an alcohol compound (e.g. methanol, and ethanol).

The reaction is performed usually in the presence of a solvent. Examples of the solvent used in the reaction include halogenated hydrocarbons such as carbon tetrachloride and the like, halogenated aromatic hydrocarbons such as chlorobenzene, bromobenzene and the like, aromatic hydrocarbons such as toluene, xylene and the like, acid amides such as N,N-dimethylformamide and the like and a mixture thereof.

At the reaction, the azide compound is used usually at a ratio of 1 to 5 moles per 1 mole of the compound represented by the formula (IV), and the alcohol compound is used usually at a ratio of 1 mole per 1 mole of the azide compound.

When the compound represented by the formula (IV) is reacted with the azide compound, a reaction temperature is usually in a range of −20 to 100° C., and a reaction time is usually in a range of 0.1 to 24 hours. When the resulting product is reacted with the alcohol compound, a reaction temperature is usually in a range of −20 to 10° C., and a reaction time is usually in a range of 0.1 to 24 hours.

After completion of the reaction, the compound represented by the formula (V-1) can be isolated by performing a post-treatment procedure such as the solid produced in the reaction mixture being collected by filtration, washing the solid with an organic solvent, drying and so on. The isolated compound represented by the formula (V-1) can be further purified by a procedure such as chromatography, recrystallization and the like. Alternatively, the compound represented by the formula (V-1) can be also prepared by the method shown in Tetrahedron Letters No. 4, pp. 243-246, 1976.

Step (1-2)

A compound represented by the formula (VI-1) can be prepared by reacting a compound represented by the formula (V-1) with a compound represented by the formula (X):

$R^{11}$—X (X)

[wherein $R^{11}$ is as defined above, and X represents a leaving group such as a halogen atom (e.g. chlorine atom, bromine atom and iodine atom), a sulfonyloxy group (e.g. methanesulfonyloxy group, methoxysulfonyloxy group, and p-toluenesulfonyloxy group) and the like] in the present of a base.

The reaction is usually performed in the presence of a solvent. Examples of the solvent used in the reaction include ketones such as acetone, ethyl methyl ketone and the like, halogenated aromatic hydrocarbons such as chlorobenzene, bromobenzene and the like, aromatic hydrocarbons such as toluene, xylene and the like, acid amides such as N,N-dimethylformamide and the like, ethers such as tetrahydrofuran, 1,4-dioxane and the like, nitriles such as acetonitrile and the like, and a mixture thereof.

Examples of the compound represented by the formula (X) which is used in the reaction include methyl iodide, methyl bromide, dimethyl sulfate, ethyl iodide, propyl iodide, and chloromethyl ethyl ether.

Examples of the base used in the reaction include carbonates such as potassium carbonate, cesium carbonate and the like and alkali metal hydrides such as sodium hydride, potassium hydride and the like.

At the reaction, the compound represented by the formula (X) is used usually at a ratio of 1 to 5 moles per 1 mole of the compound represented by the formula (VI-1), and the base is usually used at a ratio of 1 to 5 mole per 1 mole of the compound represented by the formula (VI-1).

A reaction temperature in the reaction is usually in a range of −20 to 150° C., and a reaction time is usually in a range of 0.1 to 24 hours.

After completion of the reaction, the compound represented by the formula (VI-1) can be isolated by performing the following post-treatment procedure.

The reaction mixture is cooled to room temperature, and filtered, the filtrate is concentrated under reduced pressure, and the resulting solid is washed with an organic solvent, and dried;

Water is added to the reaction mixture, this is extracted with an organic solvent, and the organic layer is concentrated.

The isolated compound represented by the formula (VI-1) may be further purified by a procedure such as chromatography, recrystallization and the like.

Step (1-3)

A compound represented by the formula (II-1) can be prepared by reacting a compound represented by the formula (VI-1) with dialkyl malonate represented by the formula:

$CH_2(COOR^4)_2$ (wherein $R^4$ is as defined above)
in the presence of a base.

The reaction is usually performed in the presence of a solvent. Examples of the solvent used in the reaction include ethers such as tetrahydrofuran, 1,4-dioxane and the like, halogenated aromatic hydrocarbons such as chlorobenzene, bromobenzene and the like, aromatic hydrocarbons such as toluene, xylene and the like, acid amides such as N,N-dimethylformamide and the like, and a mixture thereof.

Examples of the dialkyl malonate represented by the formula $CH_2(COOR^4)_2$ used in the reaction include dimethyl malonate, and diethyl malonate.

Examples of the base used in reaction include:
metal alkoxides represented by the formula:

$$NaOR^4$$

(wherein $R^4$ is as defined above), and alkali metal hydrides such as sodium hydride, potassium hydride and the like.

At the reaction, the dialkyl malonate is used usually at a ratio of 1 to 5 moles per 1 mole of the compound represented by the formula (VI-1), and the base is used usually at a ratio of 1 to 5 moles per 1 mole of the compound represented by the formula (VI-1).

A temperature in the reaction is usually in a range of −10 to 150° C., and a reaction time is usually in a range of 0.1 to 24 hours.

After completion of the reaction, the compound represented by the formula (II-1) can be isolated by performing a post-treatment procedure, such as the reaction mixture being cooled to room temperature, adding acidic water such as dilute hydrochloric acid and the like to the reaction mixture to make the aqueous layer acidic, extracting this with an organic solvent, drying and concentrating the organic layer, and so on. The isolated compound represented by the formula (II-1) may be further purified by a procedure such as chromatography, recrystallization and the like.

In addition, a compound represented by the formula (II-2) among the compound represented by the formula (II) can be prepared, for example, according to the following scheme.

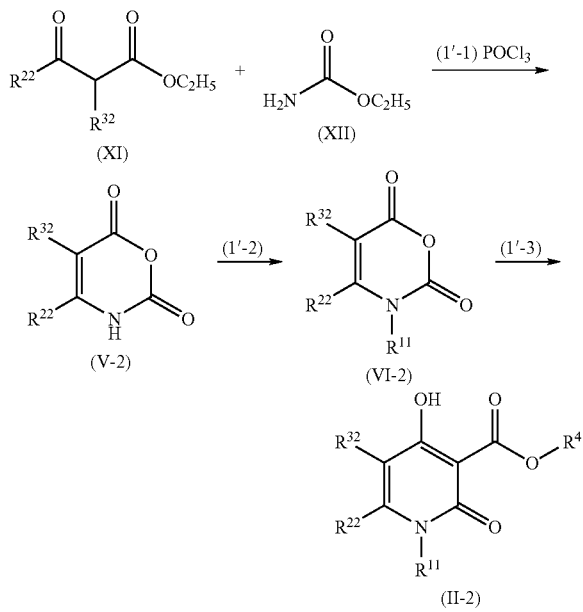

[wherein Q, $R^{11}$ and $R^4$ are as defined above, $R^{22}$ represents a C1-C3 alkyl group, $R^{32}$ represents a halogen atom, and $R^4$ represents a C1-C10 alkyl group]

Step (1'-1)

A compound represented by the formula (V-2) can be prepared according to the method described in Tetrahedron Letters No. 4, pp 243-246, 1976.

A step (1'-2) and a step (1'-3) are performed as in the step (1-2) and the step (1-3).

(Reference Process 2)

The compound represented by the formula (II) can be also prepared according to the following scheme.

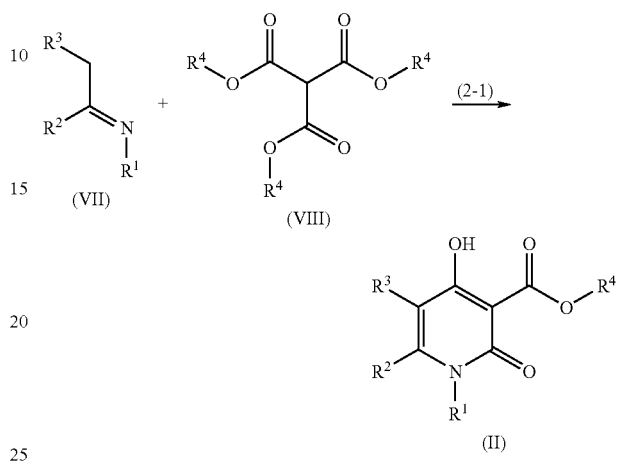

[wherein $R^1$, $R^2$, $R^3$, $R^4$ and Q are as defined above]

Step (2-1)

The compound represented by the formula (II) can be prepared by reacting a compound represented by the formula (VII) with a compound represented by the formula (VIII).

The reaction can be performed usually in the absence of a solvent. Alternatively, the reaction may be performed in the presence of a solvent while an alcohol compound produced accompanying a reaction is removed by azeotropy and the like. Examples of the solvent used in the reaction include halogenated aromatic hydrocarbons such as chlorobenzene, bromobenzene and the like, aromatic hydrocarbons such as toluene, xylene and the like, acid amides such as N,N-dimethylformamide and the like, and a mixture thereof.

At the reaction, the compound represented by the formula (VIII) is used usually at a ratio of 1 to 50 moles per 1 mole of the compound represented by the formula (VII).

A reaction temperature in the reaction is usually in a range of 100 to 250° C., and a reaction time is usually in a range of 0.1 to 24 hours.

After completion of the reaction, the compound represented by the formula (II) can be isolated, for example, by performing the following post-treatment procedure.

The reaction mixture is cooled to room temperature, the resulting solid is filtered, and the solid is washed with an organic solvent, and dried;

After the reaction mixture is cooled to room temperature, water is added to the reaction mixture, this is extracted with an organic solvent, and the organic layer is concentrated.

The isolated compound represented by the formula (II) may be further purified by a procedure such as chromatography, recrystallization and the like.

(Reference Process 3)

Among the compound represented by the formula (XIII), a compound represented by the formula (XIII-1) can be prepared from a compound represented by the formula (XVII) according to the following scheme.

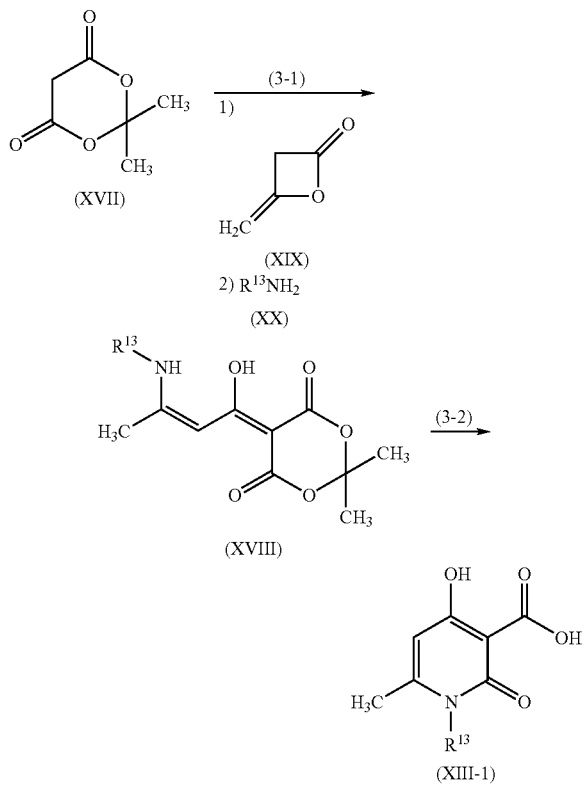

[wherein $R^{13}$ represents a C1-C3 alkyl group]

(Step 3-1)

A compound represented by the formula (XVIII) can be prepared by reacting a compound represented by the formula (XVII) with diketene represented by the formula (XIX) in the presence of tertiary amine or pyridines (first stage), and reacting the resulting product with a compound represented by the formula (XX) (second stage).

Each reaction is usually performed in the presence of a solvent. Examples of the solvent used in the reaction include nitrites such as acetonitrile, propionitrile and the like, ethers such as diethyl ether, t-butyl methyl ether, tetrahydrofuran, 1,4-dioxane and the like, halogenated aromatic hydrocarbons such as chlorobenzene, bromobenzene and the like, aromatic hydrocarbons such as toluene, xylene and the like, and a mixture thereof.

In the reaction at the first stage, diketene represented by the formula (XIX) is used usually at a ratio of 1 mole per 1 mole of the compound represented by the formula (XVII).

In the reaction at the first stage, examples of the tertiary amine used include triethylamine and tri-n-propylamine; examples of pyridines include pyridine and 4-dimethylaminopyridine. In the reaction at the first stage, tertiary amine or pyridines is used usually at a ratio of 1 mole per 1 mole of the compound represented by the formula (XVII).

A reaction temperature at the first stage is usually in a range of 0 to 40° C., and a reaction time is usually in a range of 0.1 to 24 hours.

The reaction mixture obtained by the reaction at the first stage is usually used as it is in the reaction at the second stage.

The reaction at the second stage is usually performed by mixing a reaction mixture obtained at the first stage and a compound represented by the formula (XX).

In the reaction at the second stage, the compound represented by the formula (XX) is usually used at a ratio of 2 mole per 1 mole of the compound represented by the formula (XVII).

A reaction temperature in the reaction at the second stage is usually in a range of 0 to 40° C., and a reaction time is usually in a range of 0.1 to 24 hours.

After completion of the reaction at the second stage, the compound represented by the formula (XVIII) can be isolated by performing a post-treatment procedure, such as by adding an acid (e.g. dilute hydrochloric acid, dilute sulfuric acid) to the reaction mixture, and collecting the resultant crystal by filtration, drying and so on. The isolated compound represented by the formula (XVIII) may be further purified by a procedure such as chromatography, recrystallization and the like.

(Step 3-2)

A compound represented by the formula (XIII-1) can be prepared by retaining a compound represented by the formula (XVIII) at 40 to 120° C. for 0.1 to 24 hours.

The procedure is usually performed in the presence of a solvent. Examples of the solvent used in the procedure include nitrites such as acetonitrile, propionitrile and the like, ethers such as t-butyl methyl ether, tetrahydrofuran, 1,4-dioxane and the like, halogenated aromatic hydrocarbons such as chlorobenzene, bromobenzene and the like, aromatic hydrocarbons such as toluene, xylene and the like, and a mixture thereof.

After disappearance of the compound represented by the formula (XVIII) is confirmed by an analysis means such as thin layer chromatography and the like, the compound represented by the formula (XIII-1) can be isolated by performing a post-treatment procedure, such as addition of the resulting mixture to water, extraction this with an organic solvent, concentration of an organic layer and the like. The isolated compound represented by the formula (XIII-1) may be further purified by a procedure such as chromatography, recrystallization and the like.

(Reference Process 4)

Among a compound represented by the formula (XIII), a compound represented by the formula (XIII-2) can be prepared by reacting a compound represented by the formula (XVIII) with a halogenating agent at −10 to 30° C. (first stage) and retaining the resulting product at 40 to 120° C. for 0.1 to 24 hours (second stage).

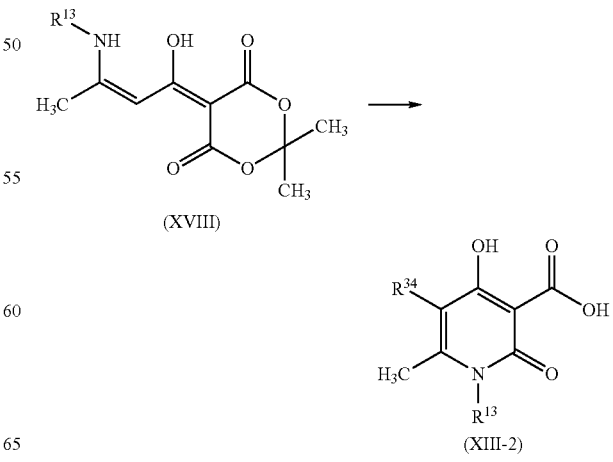

[wherein $R^{34}$ represents a halogen atom, and $R^{13}$ is as defined above]

The reaction at the first stage is usually performed in the presence of a solvent. Examples of the solvent used in the reaction include nitrites such as acetonitrile, propionitrile and the like, ethers such as diethyl ether, t-butyl methyl ether, tetrahydrofuran, 1,4-dioxane and the like, halogenated aromatic hydrocarbons such as chlorobenzene, bromobenzene and the like, aromatic hydrocarbons such as toluene, xylene and the like, and a mixture thereof.

Examples of the halogenating agent used in the reaction at the first stage include N-fluoropyridinium salt such as N,N'-difluoro-2,2'-bipyridinium bis(tetrafluoroborate) and the like, and N-halogenosuccinimides such as N-chlorosuccinimide, N-bromosuccinimide, N-iodosuccinimide and the like.

At the reaction, the halogenating agent is usually used at a ratio of 0.5 to 2 moles per 1 mole of the compound represented by the formula (XVIII).

A reaction temperature in the reaction at the first stage is usually in a range of −10 to 30° C. and a reaction time is usually in a range of 0.1 to 5 hours.

The reaction mixture obtained in the reaction at the first stage can be usually used as it is in a procedure at the second stage.

The procedure at the second stage is performed usually by retaining the reaction mixture obtained in the first stage at 40 to 120° C.

Thereafter, the compound represented by the formula (XIII-2) can be isolated by performing a post-treatment procedure, such as by adding the reaction mixture to water, extracting with an organic solvent, concentration of the organic layer and the like. The isolated compound represented by the formula (XIII-2) may be further purified by a procedure such as chromatography, recrystallization and the like.

The compound represented by the formula (III) is commercially available or can be synthesized by the known methods (e.g. methods described in Indian Journal of Chemistry, Section B: Organic Chemistry Including Medicinal Chemistry (1998), 37B(1), 84p, Bioorganic & Medicinal Chemistry Letters (2002), 12(16), 2221-2224 p, JP-B No. 52-009736, Journal of Organic Chemistry (1994), 59(24), 7299-7305 p, Phosphorus, Sulfur and Silicon and the Related Elements (2002), 177(11), 2651-2659 p, Bioorganic & Medicinal Chemistry (2001), 9(12), 3231-3241, Chemische Berichte (1960), 93, 2190-2097 p, "The Chemistry of Heterocyclic Compounds (John Wiley & Sons, Inc.)").

The compounds represented by the formula (IV), the compounds represented by the formula (VII), the compounds represented by the formula (VIII), the compounds represented by the formula (X) and dialkyl malonate are commercially available or can be synthesized using the known methods.

Examples of a plant disease which can be controlled by the present compound include the following diseases:

*Pyricularia oryzae* and *Cochliobolus miyabeanus* and *Rhizoctonia solani* of rice;
*Erysiphe graminis, Gibberella zeae, Fusarium graminearum, Fusarium culmorum, F. avenaceum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Gaeumannomyces graminis*, of wheat and barley;
*Diaporthe citri, Elsinoe fawcetti, Penicillium digitatum* and *P. italicum* of citrus; *Sclerotinia mali, Valsa mali, Podosphaera leucotricha, Alternaria mali* and *Venturia inaequalis* of apple; *Venturia nashicola, V. pirina, Alternaria kikuchiana* and *Gymnosporangium haraeanum* of pear;
*Sclerotinia cinerea, Cladosporium carpophilum* and *Phomopsis* sp. of peach; *Elsinoe ampelina, Glomerella cingulata, Uncinula necator, Phakopsora ampelopsidis, Guignardia bidwellii* and *Plasmopara viticola*, of grape; *Gloeosporium kaki, Cercospora kaki* and *Mycosphaerella nawae* of Japanese persimmon;
*Colletotrichum lagenarium, Sphaerotheca fuliginea, Mycosphaerella melonis, Fusarium oxysporum, Pseudoperonospora cubensis, Phytophthora* sp. and *Pythium* sp. of gourd;
*Alternaria solani, Cladosporium fulvum* and *Phytophthora infestans* of tomato;
*Phomopsis vexans* and *Erysiphe cichoracearum*, of eggplant; *Alternaria japonica* and *Cercosporella brassicae* of Cruciferae vegetables;
*Puccinia allii* of leek; *Cercospora kikuchii, Elsinoe glycines, Diaporthe phaseolorum* var. *sojae* and *Phakospora pachrhizii* of soybean; *Colletotrichum lindemthianum* of kidney bean; *Cercospora personata* and *Cercospora arachidicola* of peanut; *Erysiphe pisi* of pea; *Alternaria solani* and *Phytophthora infestans* of potato; *Sphaerotheca humuli* of strawberry; *Exobasidium reticulatum* and *Elsinoe leucospila* of tea; *Alternaria longipes, Erysiphe cichoracearum, Colletotrichum tabacum, Peronospora tabacina* and *Phytophthora nicotianae* of tobacco; *Cercospora beticola* of sugar beet; *Diplocarpon rosae* and *Sphaerotheca pannosa* of rose; *Septoria chrysanthemi*-indici and *Puccinia horiana* of chrysanthemum; *Botrytis cinerea* and *Sclerotinia sclerotiorum* of various crops; *Sclerotinia homeocarpaa* and *Rhizoctonia solani* of lawn.

The plant disease controlling agent of the present invention may be the present compound itself, but usually, the agent contains the present compound, and an inert carrier such as a solid carrier, a liquid carrier and the like, and is formulated in preparations by further mixing a surfactant, and other adjuvant for preparations. Examples of such the preparations includes emulsifiable concentrates, wettable powders, water dispersible granule, emulsion preparations, flowable preparations, dusts, and granules. These preparations contain the present compound as an active ingredient usually at 0.1 to 90% in terms of ratio by weight.

Examples of the solid carrier used upon formulating the preparations include fine powders and particles of minerals such as kaolin clay, attapulgite clay, bentonite, montmorillonite, acid clay, pyrophyllite, talc, diatomaceous earth, calcite and the like, natural organics such as corncob powders, walnut shell flour and the like, synthetic organics such as urea and the like, salts such as calcium carbonate, ammonium sulfate and the like, synthetic inorganic substances such as synthetic hydrous silicon oxide and the like, and the examples of the liquid carrier include aromatic hydrocarbons such as xylene, alkylbenzene, methylnaphthalene and the like, alcohols such as 2-propanol, ethylene glycol, propylene glycol, ethylene glycol monomethyl ether and the like, ketones such as acetone, cyclohexanone, isophorone and the like, vegetable oils such as soybean oil, cottonseed oil and the like, aliphatic hydrocarbons, esters, dimethyl sulfoxide, acetonitrile, and water.

Examples of the surfactant includes anionic surfactants such as alkylsulfate ester salt, alkylarylsulfonate salt, dialkylsulfosuccinate salt, polyoxyethylene alkyl aryl ether phosphate ester salt, ligninsulfonate salt, naphathalene sulfonate formaldehyde polycondensate and the like, and noinic surfactants such as polyoxyethylene alkyl aryl ether, polyoxyethylene alkyl polyoxypropylene block copolymer, sorbitan fatty acid ester and the like.

Examples of other adjuvant for preparations include water-soluble polymers such as polyvinyl alcohol, polyvinylpyrrolidone and the like, polysaccharides such as gum arabic, alginic acid and a salt thereof, CMC (carboxymethylcellulose), xanthan gum and the like, inorganic substances such as aluminum magnesium silicate, alumina sol and the like, preservative, coloring agent, and stabilizers such as PAP (acidic isopropyl phosphate), BHT and the like.

The plant disease controlling agent of the present invention is used, for example, for protecting a plant against a plant disease by foliage treatment of the plant, or is used for protecting a plant growing on a soil against a plant disease by treating the soil. When the plant disease controlling agent of the present invention is used by foliage-treating a plant, or when the agent is used by treating a soil, the amount of treatment varies depending on a kind of a crop which is a plant to be controlled, a kind of a disease to be controlled, an infestation level of a disease to be controlled, a preparation form, a treating term, weather condition and the like, and the amount in terms of the present compound per 10000 $m^2$ is usually 1 to 5000 g, preferably 5 to 1000 g.

In the case of emulsifiable concentrates, wettable powders, flowable preparations and the like, a plant is usually treated by diluting the agent with water, followed by spraying. A concentration of the present compound is usually in a range of 0.0001 to 3% by weight, preferably in a range of 0.0005 to 1% by weight. In the case of dusts, granules and the like, a plant is treated with the agent without dilution.

Alternatively, the plant disease controlling agent of the present invention may be used by a treating method such as seed disinfection. Examples of the method of disinfecting a seed include a method of immersing a plant seed in a plant disease controlling agent of the present invention which has been prepared so that a concentration of the present compound is adjusted to 1 to 1000 ppm, a method of spraying or applying the plant disease controlling agent of the present invention having a concentration of the present compound 1 to 1000 ppm on plant seeds, and a method of coating plant seeds with the plant disease controlling agent of the present invention which has been formulated into powders.

The plant disease controlling method of the present invention is usually performed by treating a plant which is expected to develop a disease or a soil where the plant grows, and/or treating a plant which is confirmed to have developed a disease or a soil where the plant grows with an effective amount of the plant disease controlling agent of the present invention.

The plant disease controlling agent of the present invention is usually used as a plant disease controlling agent for horticulture, i.e., a plant disease controlling agent for controlling a plant disease in plowed field, paddy, orchard, tea garden, meadow, lawn and so on.

The plant disease controlling agent of the present invention may be used (mixed or combined) in conjunction with other fungicides, insecticides, acaricides, nematicides, herbicides, plant growth controlling agents and/or fertilizers.

Examples of an active ingredient of such other fungicides include chlorothalonil, fluazinam, dichlofluanid, fosetyl-Al, cyclic imido derivatives (captan, captafol, folpet etc.), dithiocarbamate derivatives (maneb, mancozeb, thiram, ziram, zineb, propineb etc.), inorganic or organic copper derivatives (basic copper sulfate, copper oxychloride, copper hydroxide, oxine copper etc.), acylalanine derivatives (metalaxyl, furalaxyl, ofurace, cyprofuram, benalaxyl, oxadixyl etc.), strobilurin compounds (kresoxim-methyl, azoxystrobin, trifloxystrobin, picoxystrobin, pyraclostrobin, dimoxystrobin, fluoxastrobin, metominostrobin etc.), anilinopyrimidine derivatives (cyprodinil, pyrimethanil, mepanipyrim etc.), phenylpyrrole derivatives (fenpiclonil, fludioxonil etc.), imide derivatives (procymidone, iprodione, vincrozolin etc.), benzimidazole derivatives (carbendazim, benomyl, thiabendazol, thiophanate-methyl etc.), amine derivatives (fenpropimorph, tridemorph, fenpropidin, spiroxamine etc.), azole derivatives (propiconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol etc.), cymoxanil, dimethomorph, famoxadone, fenamidone, iprovalicarb, benthiavalicarb, cyazofamid, picobenzamid, mandipropamide, zoxamide, ethaboxam, boscalid, pyribencarb, fluopicolide, fenhexamid, quinoxyfen, proquinazid, diethofencarb, acibenzolar-S-methyl, guazatine and penthiopyrad.

Examples of the present compound include the following compounds.

Carboxamide compounds represented by the following formulas (i) to (xxviii):

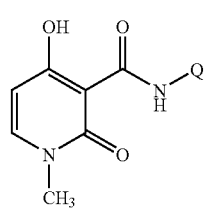
(i)

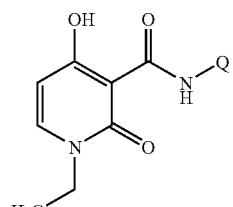
(ii)

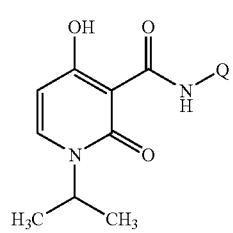
(iii)

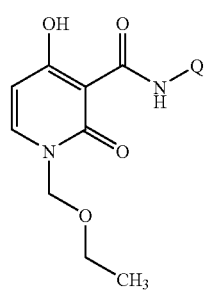
(iv)

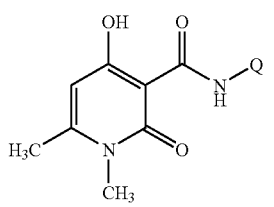 (v)
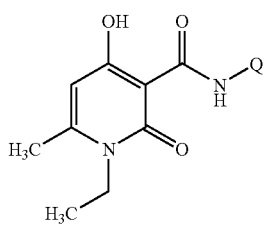 (vi)
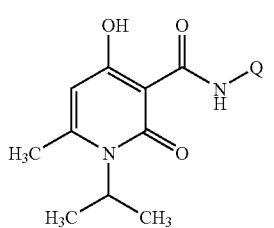 (vii)
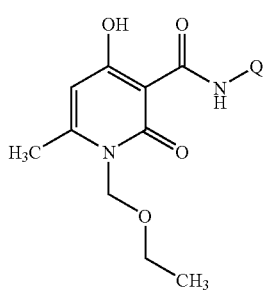 (viii)
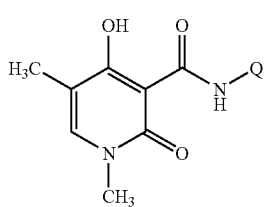 (ix)
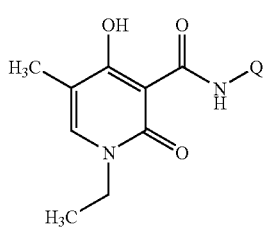 (x)
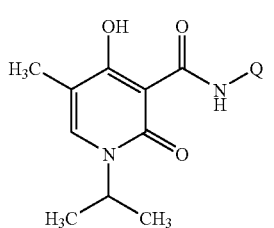 (xi)
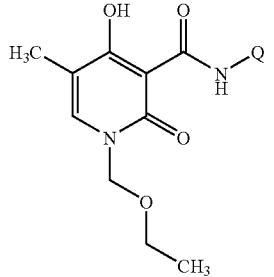 (xii)
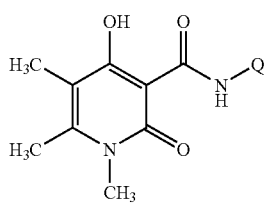 (xiii)
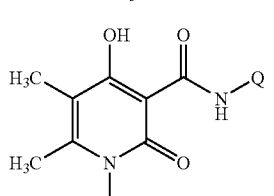 (xiv)
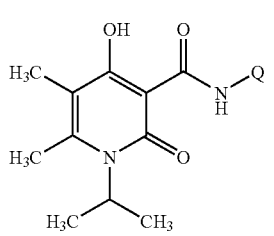 (xv)
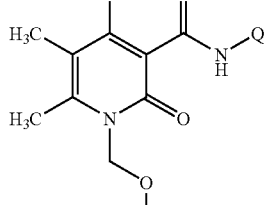 (xvi)
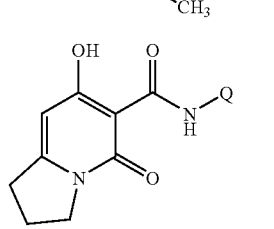 (xvii)
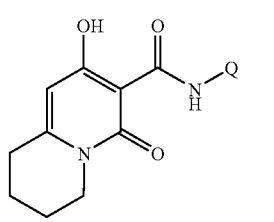 (xviii)

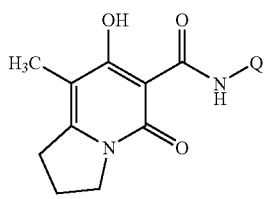
(xix)

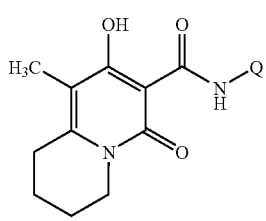
(xx)

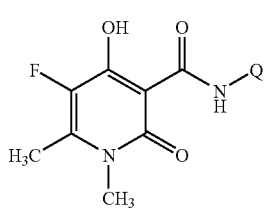
(xxi)

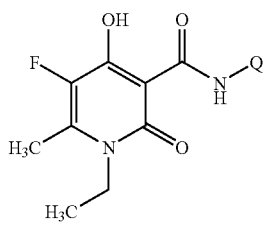
(xxii)

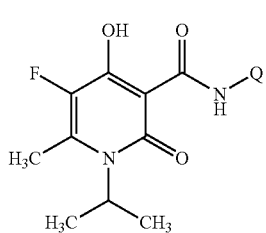
(xxiii)

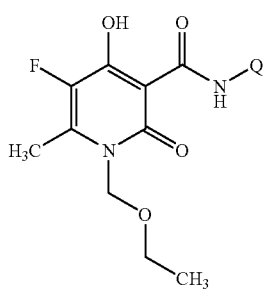
(xxiv)

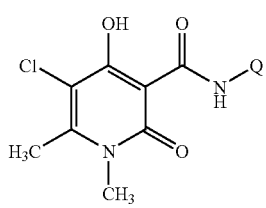
(xxv)

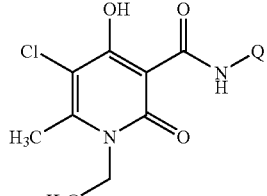
(xxvi)

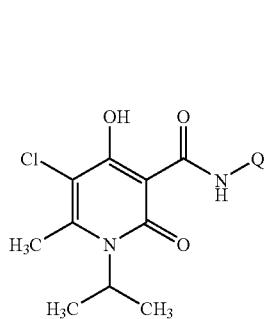
(xxvii)

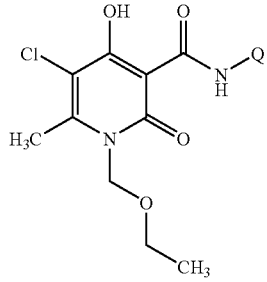
(xxviii)

In the formulas (i) to (xxviii), Q is any of the following groups.

A 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a 5-chloro-2-pyrimidinyl group, a 2-chloro-5-pyrimidinyl group, a 5-chloro-2-pyrazinyl group, a 6-chloro-3-pyridazinyl group, a 5-methyl-2-pyrimidinyl group, a 2-methyl-5-pyrimidinyl group, a 5-methyl-2-pyrazinyl group, a 6-methyl-3-pyridazinyl group, a 5-trifluoromethyl-2-pyrimidinyl group, a 2-methoxy-5-pyrimidinyl group, a 5-cyano-2-pyrazinyl group, a 6-nitro-3-pyridazinyl group, a quinoxalin-2-yl group, a quinazolin-2-yl group, a cinnolin-3-yl group, a 6-chloro-2-pyrazinyl group, a 6-methoxy-4-pyrimidinyl group, a 4-methyl-2-pyrimidinyl group, a 6-methoxy-3-pyridazinyl group, a 6-bromo-3-pyridazinyl group, a 6-cyano-3-pyridazinyl group, a 6-methylthio-3-pyridazinyl group, a 6-methoxycarbonylmethylthio-3-pyridazinyl group, a 5-bromo-2-pyrimidinyl group, a 6-ethyl-3-pyridazinyl group, a 6-propyl-3-pyridazinyl group, a 2-ethoxy-5-pyrimidinyl group, a 6-ethoxy-3-pyridazinyl group, a 6-ethylthio-3-pyridazinyl group, a 6-ethoxycarbonylmethylthio-3-pyridazinyl group, a 5-fluoro-2-pyrimidinyl group, a 2-fluoro-5-pyrimidinyl group, a 5-fluoro-2-pyrazinyl group, a 6-fluoro-3-pyridazinyl group, a 2-bromo-5-pyrimidinyl group, a 5-bromo-2-pyrazinyl group, a 5-cyano-2-pyrimidinyl group and a 2-cyano-5-pyrimidinyl group.

Examples of aspects of the intermediate for the present compound include the following compounds:

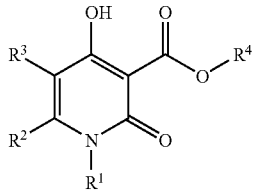

(II)

A compound in which $R^1$ is a C1-C3 alkyl group or a C2-C5 alkoxyalkyl group, $R^2$ is a hydrogen atom or a C1-C3 alkyl group, and $R^3$ is a hydrogen atom, a halogen atom or a C1-C3 alkyl group in the formula (II).

A compound in which $R^1$ and $R^2$ are bound to each other at an end to be a C3-C4 alkylene group, and $R^3$ is a hydrogen atom, a halogen atom or a C1-C3 alkyl group in the formula (II).

A compound in which $R^1$ is a C1-C3 alkyl group, $R^2$ is a hydrogen atom or a C1-C3 alkyl group, and $R^3$ is a hydrogen atom or a C1-C3 alkyl group in the formula (II).

A compound in which $R^1$ is a C1-C3 alkyl group, $R^2$ is a hydrogen atom or a C1-C3 alkyl group, and $R^3$ is a halogen atom in the formula (II).

A compound in which $R^1$ is a C1-C3 alkyl group, $R^2$ is a hydrogen atom or a C1-C3 alkyl group, and $R^3$ is a fluorine atom in the formula (II).

A compound in which $R^1$ is a C1-C3 alkyl group, $R^2$ is a C1-C3 alkyl group, and $R^3$ is a fluorine atom in the formula (II).

A compound in which $R^1$ is a C1-C3 alkyl group, $R^2$ is a methyl group, and $R^3$ is a fluorine atom in the formula (II).

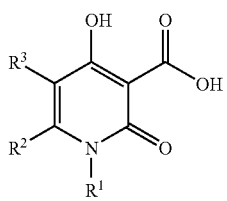

(XIII)

A compound in which $R^1$ is a C1-C3 alkyl group or a C2-C5 alkoxyalkyl group, $R^2$ is a hydrogen atom or a C1-C3 alkyl group, and $R^3$ is a hydrogen atom, a halogen atom or a C1-C3 alkyl group in the formula (XIII).

A compound in which $R^1$ and $R^2$ are bound to each other at an end to be a C3-C4 alkylene group, and $R^3$ is a hydrogen atom, a halogen atom or a C1-C3 alkyl group in the formula (XIII).

A compound in which $R^1$ is a C1-C3 alkyl group, $R^2$ is a hydrogen atom or a C1-C3 alkyl group, and $R^3$ is a hydrogen atom or a C1-C3 alkyl group in the formula (XIII).

A compound in which $R^1$ is a C1-C3 alkyl group, $R^2$ is a hydrogen atom or a C1-C3 alkyl group, and $R^3$ is a halogen atom in the formula (XIII).

A compound in which $R^1$ is a C1-C3 alkyl group, $R^2$ is a hydrogen atom or a C1-C3 alkyl group, and $R^3$ is a fluorine atom in the formula (XIII).

A compound in which $R^1$ is a C1-C3 alkyl group, $R^2$ is a C1-C3 alkyl group, and $R^3$ is a fluorine atom in the formula (XIII).

A compound in which $R^1$ is a C1-C3 alkyl group, $R^2$ is a methyl group, and $R^3$ is a halogen atom in the formula (XIII).

A compound in which $R^1$ is a C1-C3 alkyl group, $R^2$ is a methyl group, and $R^3$ is a fluorine atom in the formula (XIII).

EXAMPLES

The present invention will be explained in more detail by Preparation Examples, Formulation Examples and Test Examples, but the present invention is not limited to these Examples.

First, Preparation Examples of the present compound, and Preparation Examples of intermediate for preparing the present compound will be shown by Preparation Examples and Reference Preparation Examples.

Preparation Example 1

211 mg of ethyl 1,6-dimethyl-4-hydroxy-2-oxo-1,2-dihydropyridine-3-carboxylate and 95 mg of aminopyrazine were added to 6 ml of bromobenzene, and the mixture was stirred for 3 hours under the heat-refluxing condition. The reaction mixture was cooled to room temperature, and t-butyl methyl ether was added to the mixture. The resulting solid was collected by filtration, washed with t-butyl methyl ether, and dried to obtain 258 mg of N-(2-pyrazinyl)-1,6-dimethyl-4-hydroxy-2-oxo-1,2-dihydropyridine-3-carboxamide (hereinafter, referred to as present compound 1) represented by the formula:

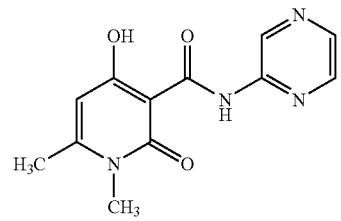

was obtained.

$^1$H-NMR (CDCl$_3$, TMS) δ (ppm): 2.40 (3H, s), 3.54 (3H, s), 6.00 (1H, s), 8.34 (2H, m), 9.52 (1H, s), 12.93 (1H, s), 14.67 (1H, s)

Preparation Example 2

Using 2-aminopyrimidine in place of aminopyrazine and according to the same manner as that of Preparation Example 1, N-(2-pyrimidinyl)-1,6-dimethyl-4-hydroxy-2-oxo-1,2-dihydropyridine-3-carboxamide (hereinafter, referred to as present compound 2) represented by the formula:

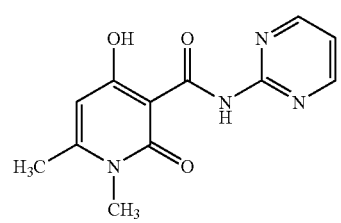

was obtained.

¹H-NMR (CDCl₃, TMS) δ (ppm): 2.45 (3H, s), 3.50 (3H, s), 6.26 (1H, s), 7.13 (2H, m), 7.48 (2H, m), 12.19 (1H, s), 13.32 (1H, s), 14.28 (1H, s)

Preparation Example 3

Using 4-aminopyrimidine in place of aminopyrazine and according to the same manner as that of Preparation Example 1, N-(4-pyrimidinyl)-1,6-dimethyl-4-hydroxy-2-oxo-1,2-dihydropyridine-3-carboxamide (hereinafter, referred to as present compound 3) represented by the formula:

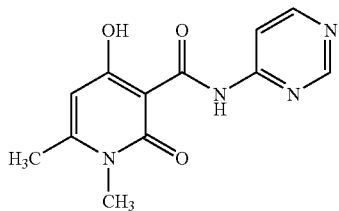

was obtained.

Preparation Example 4

Using a carboxylic acid ester compound represented by the following formula:

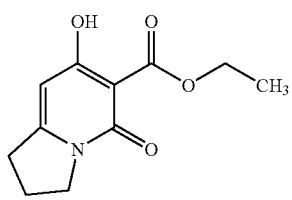

in place of ethyl 1,6-dimethyl-4-hydroxy-2-oxo-3-pyridinecarboxylate and according to the same manner as that of Preparation Example 1, a carboxamide compound (hereinafter, referred to as present compound 4) represented by the formula:

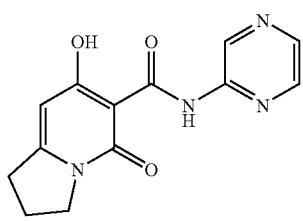

was obtained.

Preparation Example 5

Using methyl 4-hydroxy-2-oxo-1,5,6-trimethyl-1,2-dihydropyridine-3-carboxylate in place of ethyl 1,6-dimethyl-4-hydroxy-2-oxo-1,2-dihydropyridine-3-carboxylate and according to the same manner as that of Preparation Example 1, N-(2-pyrazinyl)-4-hydroxy-1,5,6-trimethyl-2-oxo-1,2-dihydropyridine-3-carboxamide (hereinafter, referred to as present compound 5) represented by the following formula:

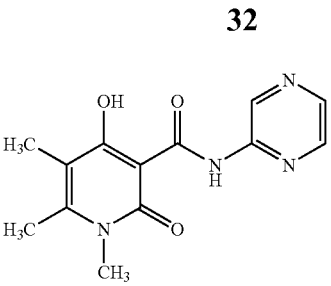

was obtained.

Preparation Example 6

Using methyl 4-hydroxy-1-methyl-2-oxo-1,2-dihydropyridine-3-carboxylate in place of ethyl 1,6-dimethyl-4-hydroxy-2-oxo-1,2-dihydropyridine-3-carboxylate and according to the same manner as that of Preparation Example 1, N-(2-pyrazinyl)-1-methyl-4-hydroxy-2-oxo-1,2-dihydropyridine-3-carboxamide (hereinafter, referred to as present compound 6) represented by the formula:

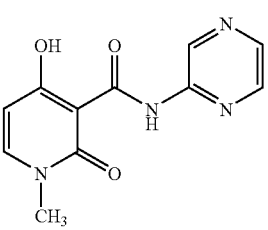

was obtained.
¹H-NMR (CDCl₃, TMS) δ (ppm): 3.50 (3H, s), 6.25 (1H, d, J=8 Hz), 8.01 (1H, d, J=8 Hz), 8.46 (2H, m), 9.39 (1H, s), 13.02 (1H, s), 14.50 (1H, s)

Preparation Example 7

Using 3-amino-1,2,4-triazine in place of aminopyrazine and according to the same manner as that of Preparation Example 1, N-(1,2,4-triazin-3-yl)-1,6-dimethyl-4-hydroxy-2-oxo-1,2-dihydropyridine-3-carboxamide (hereinafter, referred to as present compound 7) represented by the formula:

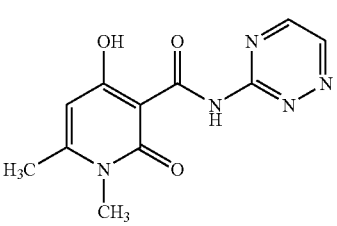

was obtained.
¹H-NMR (CDCl₃, TMS) δ (ppm): 2.42 (3H, s), 3.55 (3H, s), 6.02 (1H, s), 8.58 (1H, d, J=2 Hz), 9.05 (1H, d, J=2 Hz), 13.66 (1H, s), 14.48 (1H, s)

Preparation Example 8

Using 2-amino-1,3,5-triazine in place of aminopyrazine and according to the same manner as that of Preparation Example 1, N-(1,3,5-triazin-2-yl)-1,6-dimethyl-4-hydroxy-2-oxo-1,2-dihydropyridine-3-carboxamide (hereinafter, referred to as present compound 8) represented by the formula:

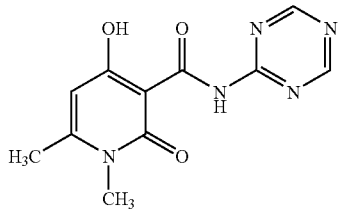

was obtained.

¹H-NMR (CDCl₃, TMS) δ (ppm): 2.42 (3H, s), 3.54 (3H, s), 6.03 (1H, s), 9.04 (2H, s), 13.48 (1H, s), 14.31 (1H, s)

Preparation Example 9

Using 2-amino-6-chloropyrazine in place of aminopyrazine and according to the same manner as that of Preparation Example 1, N-(6-chloro-2-pyrazinyl)-1,6-dimethyl-4-hydroxy-2-oxo-1,2-dihydropyridine-3-carboxamide (hereinafter, referred to as present compound 9) represented by the formula:

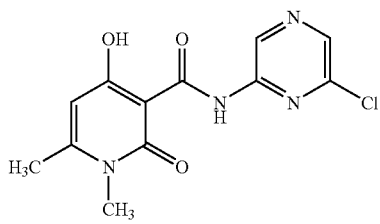

was obtained.

¹H-NMR (CDCl₃, TMS) δ (ppm): 2.41 (3H, s), 3.53 (3H, s), 6.01 (1H, s), 8.34 (1H, s), 9.45 (1H, s), 12.99 (1H, s), 14.44 (1H, s)

Preparation Example 10

Using 4-amino-6-methoxypyrimidine in place of aminopyrazine and according to the same manner as that of Preparation Example 1, N-(6-methoxy-4-pyrimidinyl)-1,6-dimethyl-4-hydroxy-2-oxo-1,2-dihydropyridine-3-carboxamide (hereinafter, referred to as present compound 10) represented by the formula:

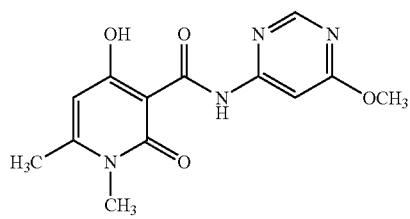

was obtained.

¹H-NMR (CDCl₃, TMS) δ (ppm): 2.39 (3H, s), 3.52 (3H, s), 3.99 (3H, s), 5.98 (1H, s), 7.57 (1H, s), 8.54 (1H, s), 12.86 (1H, s), 14.57 (1H, s)

Preparation Example 11

Using 2-amino-5-chloropyrimidine in place of aminopyrazine and according to the same manner as that of Preparation Example 1, N-(5-chloro-2-pyrimidinyl)-1,6-dimethyl-4-hydroxy-2-oxo-1,2-dihydropyridine-3-carboxamide (hereinafter, referred to as present compound 11) represented by the formula:

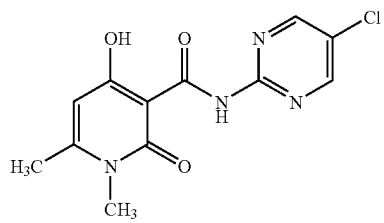

was obtained.

¹H-NMR (CDCl₃, TMS) δ (ppm): 2.40 (3H, s), 3.53 (3H, s) 6.00 (1H, s), 8.61 (2H, s), 13.33 (1H, s), 14.67 (1H, s)

Preparation Example 12

Using 3-amino-6-chloropyridazine in place of aminopyrazine and according to the same manner as that of Preparation Example 1, N-(6-chloro-3-pyridazinyl)-1,6-dimethyl-4-hydroxy-2-oxo-1,2-dihydropyridine-3-carboxamide (hereinafter, referred to as present compound 12) represented by the formula:

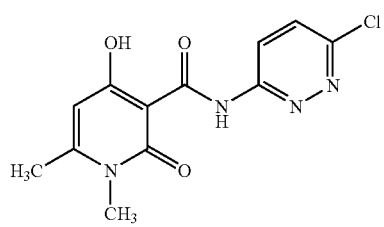

was obtained.

¹H-NMR (CDCl₃, TMS) δ (ppm): 2.41 (3H, s), 3.54 (3H, s), 6.00 (1H, s), 7.49 (1H, d, J=9 Hz), 8.50 (1H, d, J=9 Hz), 13.34 (1H, s), 14.40 (1H, s)

Preparation Example 13

Using 2-amino-4-methylpyrimidine in place of aminopyrazine and according to the same manner as that of Preparation Example 1, N-(4-methyl-2-pyrimidinyl)-1,6-dimethyl-4-hydroxy-2-oxo-1,2-dihydropyridine-3-carboxamide (hereinafter, referred to as present compound 13) represented by the formula:

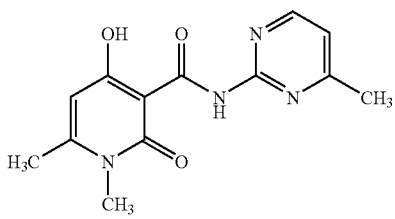

was obtained.

¹H-NMR (CDCl₃, TMS) δ (ppm): 2.39 (3H, s), 2.51 (3H, s), 3.53 (3H, s), 5.99 (1H, s), 6.91 (1H, d, J=5 Hz), 8.54 (1H, d, J=5 Hz), 13.10 (1H, s), 14.92 (1H, s)

Preparation Example 14

Using ethyl 1,5-dimethyl-4-hydroxy-2-oxo-1,2-dihydropyridine-3-carboxylate in place of ethyl 1,6-dimethyl-4-hydroxy-2-oxo-1,2-dihydropyridine-3-carboxylate and according to the same manner as that of Preparation Example 1, N-(2-pyrazinyl)-1,5-dimethyl-4-hydroxy-2-oxo-1,2-dihydropyridine-3-carboxamide (hereinafter, referred to as present compound 14) represented by the formula:

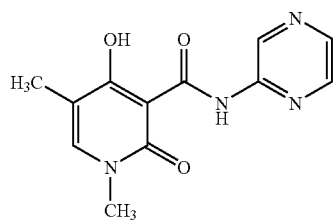

was obtained.

¹H-NMR (CDCl₃, TMS) δ (ppm): 2.06 (3H, s), 3.54 (3H, s), 7.24 (1H, s), 8.34 (2H, m), 9.52 (1H, d, J=2 Hz), 13.07 (1H, s), 14.37 (1H, s)

Preparation Example 15

Using 2-aminoquinoxaline in place of aminopyrazine and according to the same manner as that of Preparation Example 1, N-(quinoxalin-2-yl)-1,6-dimethyl-4-hydroxy-2-oxo-1,2-dihydropyridine-3-carboxamide (hereinafter, referred to as present compound 15) represented by the formula:

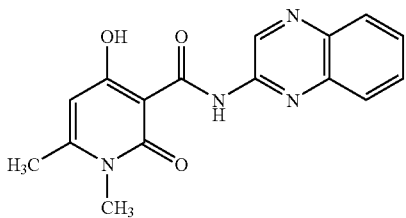

was obtained.

¹H-NMR (CDCl₃, TMS) δ (ppm): 2.42 (3H, s), 3.57 (3H, s), 6.03 (1H, s), 7.66 (1H, dd, J=6, 8 Hz), 7.72 (1H, dd, J=6, 8 Hz), 7.95 (1H, d, J=8 Hz), 8.08 (1H, d, J=8 Hz), 9.83 (1H, s), 13.17 (1H, s), 14.69 (1H, s)

Preparation Example 16

161 mg of ethyl 5-chloro-1,6-dimethyl-4-hydroxy-2-oxo-1,2-dihydropyridine-3-carboxylate and 78 mg of 2-amino-5-chloropyrimidine were added to 1.5 ml of bromobenzene, and the mixture was stirred for 4 hours under heat refluxing condition. The reaction mixture was cooled to room temperature and N-hexane was added to the reaction mixture.

The resulting solid was collected by filtration, washed with a mixture of t-butyl methyl ether and n-hexane, and dried to obtain 152 mg of N-(5-chloro-2-pyrimidinyl)-5-chloro-1,6-dimethyl-4-hydroxy-2-oxo-1,2-dihydropyridine-3-carboxamide (hereinafter, referred to as present compound 16) represented by the formula:

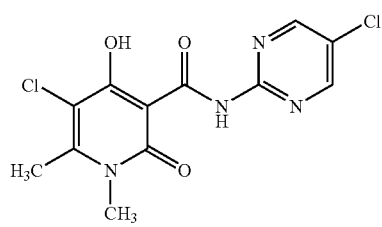

¹H-NMR (CDCl₃, TMS) δ (ppm): 2.62 (3H, s), 3.63 (3H, s), 8.63 (2H, s), 13.33 (1H, s), 15.72 (1H, s)

Preparation Example 17

168 mg of ethyl 5-chloro-1,6-dimethyl-4-hydroxy-2-oxo-1,2-dihydropyridine-3-carboxylate and 82 mg of 3-amino-6-chloropyridazine were added to 1.5 ml of bromobenzene, and the mixture was stirred for 4 hours under heat refluxing. The reaction mixture was cooled to room temperature, and n-hexane was added to the reaction mixture. The resulting solid was collected by filtration, washed with a mixture of t-butyl methyl ether and n-hexane, and dried to obtain 180 mg of N-(6-chloro-3-pyridazinyl)-5-chloro-1,6-dimethyl-4-hydroxy-2-oxo-1,2-dihydropyridine-3-carboxamide (hereafter, referred to as present compound 17) represented by the formula:

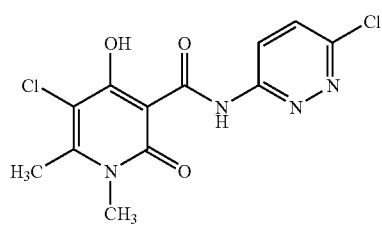

¹H-NMR (CDCl₃, TMS) δ (ppm): 2.63 (3H, s), 3.64 (3H, s) 7.51 (1H, d, J=9 Hz), 8.50 (1H, d, J=9 Hz), 13.35 (1H, s), 15.42 (1H, s)

Preparation Example 18

Using methyl 4-hydroxy-1-methyl-2-oxo-1,2-dihydropyridine-3-carboxylate in place of ethyl 1,6-dimethyl-4-hydroxy-2-oxo-1,2-dihydropyridine-3-carboxylate, and using 2-amino-5-chloropyrimidine in place of aminopyrazine and according to the same manner as that of Preparation Example 1, N-(5-chloro-2-pyrimidinyl)-1-methyl-4-hydroxy-2-oxo- 1,2-dihydropyridine-3-carboxamide (hereinafter, referred to as present compound 18) represented by the following formula:

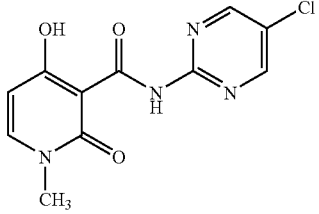

was obtained.

$^1$H-NMR (CDCl$_3$, TMS) δ (ppm): 3.56 (3H, s), 6.13 (1H, d, J=7 Hz), 7.39 (1H, d, J=7 Hz), 8.62 (2H, s), 13.28 (1H, s), 14.84 (1H, s)

Preparation Example 19

600 mg of ethyl 5-fluoro-1,6-dimethyl-4-hydroxy-2-oxo-1,2-dihydropyridine-3-carboxylate and 194 mg of 3-amino-6-chloropyridazine were added to 5 ml of bromobenzene, and the mixture was stirred at 160° C. for 4 hours. The reaction mixture was cooled to room temperature, and subjected to silica gel chromatography (chloroform:methanol=20:1). The resulting crude product was washed with a mixture of t-butyl methyl ether and n-hexane, and dried to obtain 311 mg of N-(6-chloro-3-pyridazinyl)-5-fluoro-1,6-dimethyl-4-hydroxy-2-oxo-1,2-dihydropyridine-3-carboxamide (hereinafter, referred to as present compound 19) represented by the formula:

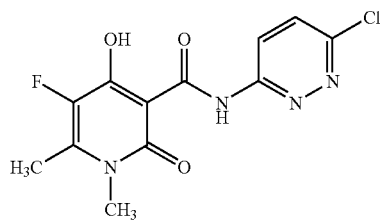

$^1$H-NMR (CDCl$_3$, TMS) δ (ppm): 2.45 (3H, d, J=3 Hz), 3.56 (3H, s), 7.51 (1H, dd, J=9, 1 Hz), 8.50 (1H, d, J=9 Hz), 13.34 (1H, s), 14.92 (1H, s)

Preparation Example 20

300 mg of 5-fluoro-1,6-dimethyl-4-hydroxy-2-oxo-1,2-dihydropyridine-3-carboxylic acid and 266 mg of carbonyldiimidazole were added to 5 ml of acetonitrile. The mixture was stirred for 1 hour under heat refluxing condition. Thereafter, 212 mg of 3-amino-6-chloropyridazine was added to the mixture, and this was further stirred for 1 hour under heat refluxing condition. The reaction mixture was cooled to room temperature and crystals were produced. The crystals were collected by filtration to obtain 250 mg of N-(6-chloro-3-pyridazinyl)-5-fluoro-1,6-dimethyl-4-hydroxy-2-oxo-1,2-dihydropyridine-3-carboxamide (present compound 19):

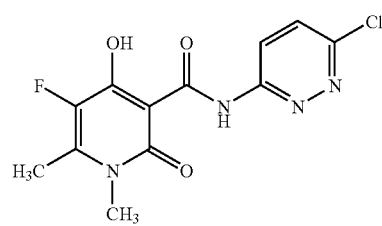

Preparation Example 21

Using 3-amino-6-methoxypyridazine in place of 3-amino-6-chloropyridazine and according to the same manner as that of Preparation Example 20, N-(6-methoxy-3-pyridazinyl)-1,6-dimethyl-5-fluoro-4-hydroxy-2-oxo-1,2-dihydropyridine-3-carboxamide (hereinafter referred to as present compound 20) represented by the formula:

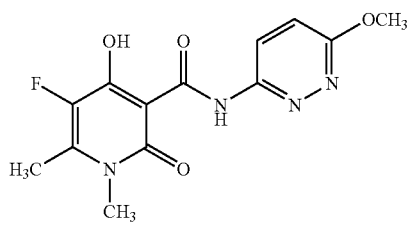

was obtained.

$^1$H-NMR (CDCl$_3$, TMS) δ (ppm): 2.42 (3H, s), 3.55 (3H, s), 4.12 (3H, s), 7.01 (1H, d, J=8 Hz), 8.37 (1H, d, J=8 Hz), 13.02 (1H, s), 15.36 (1H, br)

Preparation Example 22

Using 3-amino-6-methylpyridazine in place of 3-amino-6-chloropyridazine and according to the same manner as that of Preparation Example 20, N-(6-methyl-3-pyridazinyl)-1,6-dimethyl-5-fluoro-4-hydroxy-2-oxo-1,2-dihydropyrizine-3-carboxamide (hereinafter, referred to as present compound 21) represented by the formula:

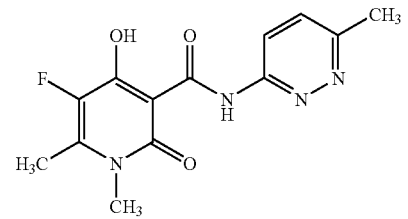

was obtained.

$^1$H-NMR (DMSO-d$_6$, TMS) δ (ppm): 2.44 (3H, s), 2.60 (3H, s), 3.50 (3H, s), 7.65 (1H, d, J=9 Hz), 8.27 (1H, d, J=9 Hz), 13.23 (1H, s)

Preparation Example 23

Using 3-amino-6-bromopyridazine in place of 3-amino-6-chloropyridazine and according to the same manner as that of Preparation Example 20, N-(6-bromo-3-pyridazinyl)-1,6-dimethyl-5-fluoro-4-hydroxy-2-oxo-1,2-dihydropyrizine-3- carboxamide (hereinafter, referred to as present compound 22) represented by the formula:

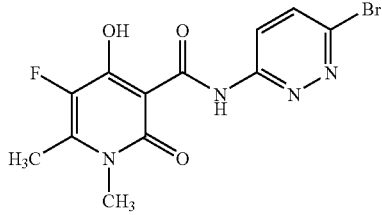

was obtained.

¹H-NMR (DMSO-d$_6$, TMS) δ (ppm): 2.45 (3H, s), 3.52 (3H, s), 7.25 (1H, s), 8.11 (1H, br), 8.48 (1H, br), 13.64 (1H, br)

Preparation Example 24

Using 3-amino-6-cyanopyridazine in place of 3-amino-6-chloropyridazine and according to the same manner as that of Preparation Example 20, N-(6-cyano-3-pyridazinyl)-1,6-dimethyl-5-fluoro-4-hydroxy-2-oxo-1,2-dihydropyrizine-3-carboxamide (hereinafter, referred to as present compound 23) represented by the formula:

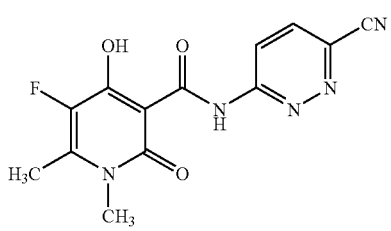

was obtained.

¹H-NMR (DMSO-d$_6$, TMS) δ (ppm): 2.46 (3H, s), 3.52 (3H, s) 8.37 (1H, d, J=9 Hz), 8.54 (1H, d, J=9 Hz), 13.73 (1H, brs)

Preparation Example 25

Using 3-amino-6-methylthiopyridazine in place of 3-amino-6-chloropyridazine and according to the same manner as that of Preparation Example 20, N-(6-methylthio-3-pyridazinyl)-1,6-dimethyl-5-fluoro-4-hydroxy-2-oxo-1,2-dihydropyridine-3-carboxamide (hereinafter, referred to as present compound 24) represented by the formula:

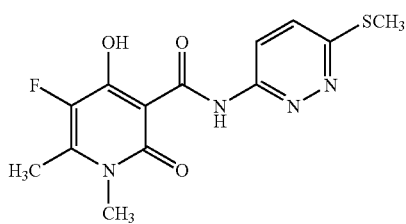

was obtained.

¹H-NMR (CDCl$_3$, TMS) δ (ppm): 2.44 (3H, s), 2.71 (3H, s), 3.55 (3H, s), 7.35 (1H, d, J=9 Hz), 8.28 (1H, d, J=9 Hz), 13.13 (1H, s), 15.21 (1H, s)

Preparation Example 26

Using 3-amino-6-(methoxycarbonylmethylthio)pyridazine in place of 3-amino-6-chloropyridazine and according to the same manner as that of Preparation Example 20, N-(6-methoxycarbonylmethylthio-3-pyridazinyl)-1,6-dimethyl-5-fluoro-4-hydroxy-2-oxo-1,2-dihydropyrizine-3-carboxamide (hereinafter, referred to as present compound 25) represented by the formula:

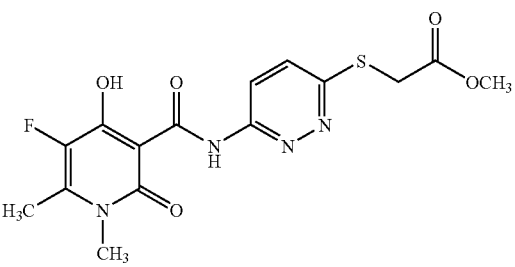

was obtained.

¹H-NMR (DMSO-d$_6$, TMS) δ: 2.44 (3H, s), 3.50 (3H, s), 3.66 (3H, s), 4.18 (2H, s), 7.77 (1H, d, J=9 Hz), 8.24 (1H, d, J=9 Hz), 13.24 (1H, brs), 14.80 (1H, brs)

Preparation Example 27

Using 2-amino-5-bromopyrimidine in place of 3-amino-6-chloropyridazine and according to the same manner as that of Preparation Example 20, N-(5-bromo-2-pyrimidinyl)-1,6-dimethyl-5-fluoro-4-hydroxy-2-oxo-1,2-dihydropyridine-3-carboxamide (hereinafter, referred to as present compound 26) represented by the formula:

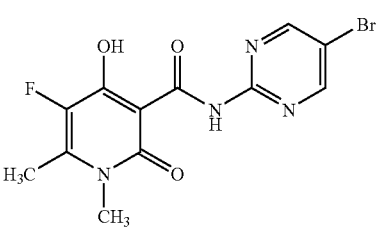

was obtained.

¹H-NMR (CDCl$_3$, TMS) δ (ppm): 2.46 (3H, s), 3.53 (3H, s), 9.00 (2H, s), 13.38 (1H, s), 15.39 (1H, s)

Then, Reference Preparation Examples for preparating intermediates of the present compound will be described.

Reference Preparation Example 1

At room temperature, to a mixture of 5.0 g of maleic anhydride and 20 ml of benzene was added 7.9 ml of trimethylsilylazide. The mixture was stirred at 50 to 60° C. for 3 hours. After the reaction mixture was cooled to room temperature, 4.5 ml of ethanol was added, followed by further stirring for 3 hours. The resulting solid was collected by filtration, and washed with diethyl ether to obtain 300 mg of 2H-1,3-oxazine-2,6(3H)-dione represented by the formula:

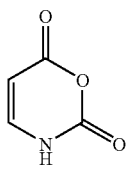

$^1$H-NMR (CD$_3$SOCD$_3$, TMS) δ (ppm): 5.62 (1H, d, J=8 Hz), 7.66 (1H, d, J=8 Hz), 11.55 (1H, s)

Reference Preparation Example 2

At room temperature, to a mixture of 44.8 g of citraconic anhydride and 60 ml of chloroform was added 50.0 g of trimethylsilylazide. The mixture was stirred at 50 to 60° C. for 5 hours. After the reaction mixture was cooled with an ice, 25.0 g of ethanol was added, followed by further stirring for 30 minutes. The resulting solid was collected by filtration, and washed with a mixed solvent of chloroform and ethanol to obtain crude 4-methyl-2H-1,3-oxazine-2,6-(3H)-dione represented by the formula:

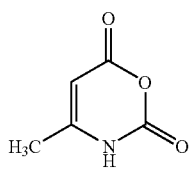

Separately, the washing solution was concentrated under reduced pressure. To the residue was added t-butyl methyl ether, followed by filtration. The resulting solid was washed with t-butyl methyl ether. The filtrate and the washing solution were combined and concentrated under reduced pressure to obtain crude 5-methyl-2H-1,3-oxazine-2,6(3H)-dione represented by the formula:

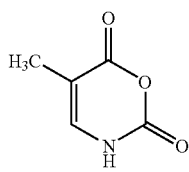

4-Methyl-2H-1,3-oxazine-2,6(3H)-dione $^1$H-NMR (CD$_3$SOCD$_3$, TMS) δ (ppm): 2.06 (3H, s), 5.50 (1H, s), 11.47 (1H, s-br)

5-Methyl-2H-1,3-oxazine-2,6(3H)-dione $^1$H-NMR (CD$_3$SOCD$_3$, TMS) δ (ppm): 1.78 (3H, s), 7.48 (1H, s), 11.47 (1H, s-br)

Reference Preparation Example 3

At room temperature, 1.50 g of 2H-1,3-oxazine-2,6(3H)-dione, 2.19 g of potassium carbonate and 3.77 g of methyl iodide were sequentially added to 30 ml of acetone, and the mixture was stirred for 10 hours under heat refluxing condition. The reaction mixture was cooled to room temperature and filtered. The filtrate was concentrated under reduced pressure, and the resulting solid was dried to obtain 1.46 g of 3-methyl-2H-1,3-oxazine-2,6(3H)-dione represented by the formula:

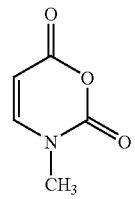

$^1$H-NMR (CD$_3$SOCD$_3$, TMS) δ (ppm): 3.26 (3H, s), 5.68 (1H, d, J=8 Hz), 7.82 (1H, d, J=8 Hz)

Reference Preparation Example 4

Using crude 4-methyl-2H-1,3-oxazine-2,6-(3H)-dione in place of 2H-1,3-oxazine-2,6(3H)-dione and according to the same manner as that of Reference Preparation Example 3, crude 3,4-dimethyl-2H-1,3-oxazine-2,6-(3H) dione represented by the formula:

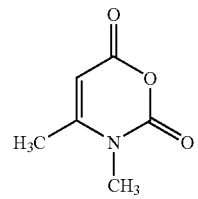

was obtained.

$^1$H-NMR (CDCl$_3$, TMS) δ (ppm): 2.27 (3H, d), 3.41 (3H, s), 5.49 (1H, d)

Reference Preparation Example 5

Using ethyl bromide in place of methyl iodide and according to the same manner as that of Reference Preparation Example 3,3-ethyl-2H-1,3-oxazine-2,6(3H)-dione represented by formula:

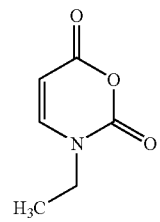

was obtained.

Reference Preparation Example 6

Using chloromethyl ethyl ether in place of methyl iodide and according to the same manner as that of Reference Preparation Example 3,3-ethoxymethyl-2H-1,3-oxazine-2,6(3H)-dione represented by the formula:

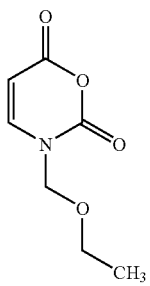

was obtained.

Reference Preparation Example 7

Using crude 5-methyl-2H-1,3-oxazine-2,6(3H)-dione in place of 2H-1,3-oxazine-2,6(3H)-dione and according to the same manner as that of Reference Preparation Example 3, crude 3,5-dimethyl-2H-1,3-oxazine-2,6(3H)-dione represented by the formula:

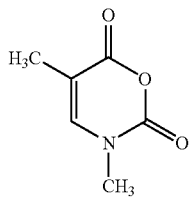

was obtained.

$^1$H-NMR (CDCl$_3$, TMS) δ (ppm): 1.94 (3H, d), 3.37 (3H, s), 6.99 (1H, q-like)

Reference Preparation Example 8

Using 4,5-dimethyl-2H-1,3-oxazine-2,6(3H)-dione represented by the formula:

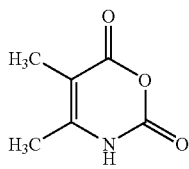

in place of 2H-1,3-oxazine-2,6(3H)-dione and according to the same manner as that of Reference Preparation Example 3, 3,4,5-trimethyl-2H-1,3-oxazine-2,6(3H)-dione represented by the formula:

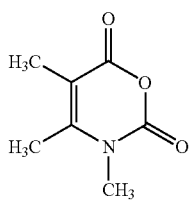

was obtained.

$^1$H-NMR (CDCl$_3$, TMS) δ (ppm): 1.97 (3H, s), 2.26 (3H, s) 3.42 (3H, s)

Reference Preparation Example 9

Under ice cooling, 568 mg of sodium hydride (60%) was added to a mixture of 181 mg of dimethyl malonate and 70 ml of N,N-dimethylformamide, and the mixture was stirred for 20 minutes. After the mixture was heated to 80° C., 1.50 g of 3-methyl-2H-1,3-oxazine-2,6(3H)-dione was added to the mixture, followed by further stirring at 120° C. for 7 hours. The reaction mixture was concentrated under reduced pressure, 2 mol/L hydrochloric acid was added to the residue, and the mixture was stirred at 60° C. for 15 minutes. The mixture was extracted with ethyl acetate. The organic layer was washed with an aqueous saturated sodium chloride solution, dried with sodium sulfate, filtered, and concentrated. The residue was subjected to silica gel column chromatography (eluent: ethyl acetate) to obtain 100 mg of methyl 4-hydroxy-1-methyl-2-oxo-1,2-dihydropyridine-3-carboxylate represented by the formula:

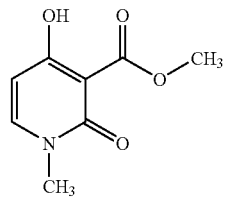

$^1$H-NMR (CDCl$_3$, TMS) δ (ppm): 3.44 (3H, s), 3.97 (3H, s), 5.97 (1H, d, J=8 Hz), 7.37 (1H, d, J=8 Hz), 13.21 (1H, s)

Reference Preparation Example 10

At room temperature, 1 ml of a solution of 0.71 g of diethyl malonate in tetrahydrofuran was added to a mixture of 0.19 g of sodium hydride and 4 ml of tetrahydrofuran, and the mixture was stirred for 20 minutes. At room temperature, 3 ml of a solution of 0.59 g of 3,4-dimethyl-2H-1,3-oxazine-2,6(3H)-dione in tetrahydrofuran was added to the mixture, followed by stirring for 2 hours under heat refluxing condition. The reaction mixture was concentrated under reduced pressure. To the residue were added 10 ml of water and 12 ml of 2 mol/L hydrochloric acid, followed by extraction with ethyl acetate. The organic layer was dried with magnesium sulfate, filtered and concentrated to obtain 0.57 g of ethyl 1,6-dimethyl-4-hydroxy-2-oxo-1,2-dihydropyridine-3-carboxylate represented by the formula:

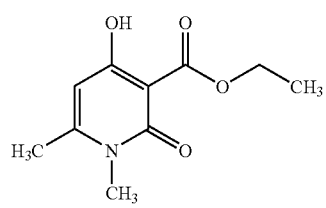

$^1$H-NMR (CDCl$_3$, TMS) δ (ppm): 1.44 (3H, t, J=7 Hz), 2.34 (3H, s), 3.45 (3H, s), 4.43 (2H, q, J=7 Hz), 5.86 (1H, s), 13.26 (1H, s)

Reference Preparation Example 11

Using 3-ethyl-2H-1,3-oxazine-2,6(3H)-dione in place of 3,4-dimethyl-2H-1,3-oxazine-2,6(3H)-dione, and using dimethyl malonate in place of diethyl malonate, and according to the same manner as that of Reference Preparation Example 10, methyl 1-ethyl-4-hydroxy-2-oxo-1,2-dihydropyridine-3-carboxylate represented by the formula:

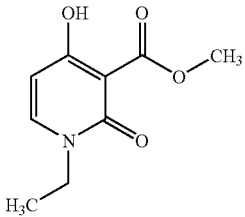

was obtained.

$^1$H-NMR (CDCl$_3$, TMS) δ (ppm): 1.33 (3H, t, J=7 Hz), 3.94 (2H, q, J=7 Hz), 3.98 (3H, s), 5.98 (1H, d, J=8 Hz), 7.37 (1H, d, J=8 Hz), 13.25 (1H, s)

Reference Preparation Example 12

Using 3-ethoxymethyl-2H-1,3-oxazine-2,6(3H)-dione in place of 3,4-dimethyl-2H-1,3-oxazine-2,6(3H)-dione and according to the same manner as that of Reference Preparation Example 10, ethyl 1-ethoxymethyl-4-hydroxy-2-oxo-1,2-dihydropyridine-3-carboxylate represented by the formula:

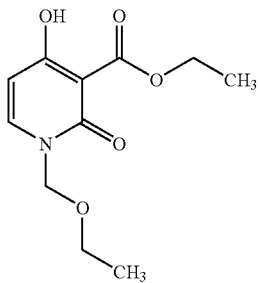

was obtained.

$^1$H-NMR (CDCl$_3$, TMS) δ (ppm): 1.20 (3H, t, J=7 Hz), 1.44 (3H, t, J=7 Hz), 3.60 (2H, q, J=7 Hz), 4.45 (2H, q, J=7 Hz), 5.30 (2H, s), 6.03 (1H, d, J=8 Hz), 7.50 (1H, d, J=8 Hz), 13.55 (1H, s)

Reference Preparation Example 13

Using 3,5-dimethyl-2H-1,3-oxazine-2,6(3H)-dione in place of 3,4-dimethyl-2H-1,3-oxazine-2,6(3H)-dione and according to the same manner as that of Reference Preparation Example 10, ethyl 1,5-dimethyl-4-hydroxy-2-oxo-1,2-dihydropyridine-3-carboxylate represented by the formula:

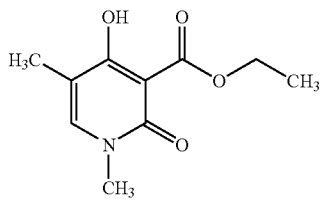

was obtained.

Reference Preparation Example 14

Using 3,4,5-trimethyl-2H-1,3-oxazine-2,6(3H)-dione in place of 3,4-dimethyl-2H-1,3-oxazine-2,6(3H)-dione, and using dimethyl malonate in place of diethyl malonate, and according to the same manner as that of Reference Preparation Example 10, methyl 4-hydroxy-2-oxo-1,5,6-trimethyl-1,2-dihydropyridine-3-carboxylate represented by the formula:

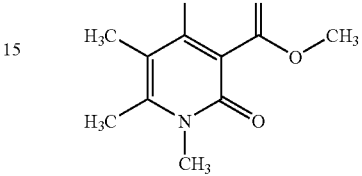

was obtained.

$^1$H-NMR (CDCl$_3$, TMS) δ (ppm): 2.05 (3H, s), 2.36 (3H, s), 3.51 (3H, s), 3.96 (3H, s), 13.83 (1H, s)

Reference Preparation Example 15

A mixture of 10.1 ml of 2-methyl-1-pyrroline and 2.27 ml of triethyl methanetricarboxylate was stirred at 200° C. for 20 hours. The reaction mixture was cooled to room temperature, and subjected to silica gel column chromatography to obtain 400 mg of carboxylic acid ester represented by the formula:

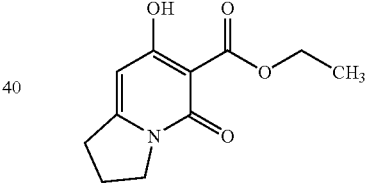

$^1$H-NMR (CDCl$_3$, TMS) δ (ppm): 1.43 (3H, t, J=7 Hz), 2.14 (2H, m), 3.06 (2H, t, J=7 Hz), 4.08 (2H, t, J=7 Hz), 4.41 (2H, q, J=7 Hz), 5.90 (1H, s), 13.35 (1H, s)

Reference Preparation Example 16

After 16.5 g of ethyl 2-chloroacetoacetate and 8.91 g of ethyl carbamate were sequentially added to 83.9 g of phosphorus oxychloride, the mixture was stirred at 90° C. for 5 hours. The reaction mixture was concentrated under reduced pressure, and toluene and water were added to the residue, followed by separation of the layers. The organic layer was extracted with water four times. The aqueous layers were collected, and extracted with ethyl acetate four times. The organic layers were collected, washed with water, dried with magnesium sulfate, filtered and concentrated. The resulting solid was washed with a mixture of t-butyl methyl ether and n-hexane and dried to obtain 5-chloro-4-methyl-2H-1,3-oxazine-2,6(3H)-dione represented by the formula:

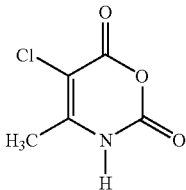

¹H-NMR (CDCl₃, TMS) δ (ppm): 2.34 (3H, s)

Reference Preparation Example 17

At room temperature, 2.11 g of 5-chloro-4-methyl-2H-1,3-oxazine-2,6(3H)-dione, 2.07 g of potassium carbonate and 1.3 ml of methyl iodide were sequentially added to 40 ml of acetone, and the mixture was stirred for 3 hours under heat refluxing condition. To the reaction mixture was added 0.5 ml of methyl iodide, and the mixture was further stirred for 2 hours under heat refluxing condition. The reaction mixture was cooled to room temperature and filtered. The filtrate was concentrated under reduced pressure. The resulting solid was dried to obtain 1.74 g of 5-chloro-3,4-dimethyl-2H-1,3-oxazine-2,6(3H)-dione represented by the formula:

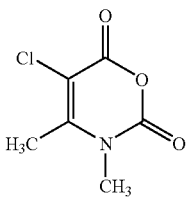

¹H-NMR (CDCl₃, TMS) δ (ppm): 2.48 (3H, s), 3.48 (3H, s)

Reference Preparation Example 18

To 0.43 g of sodium hydride (60%) was added 35 ml of tetrahydrofuran, 2.5 ml of a solution of 1.76 g of diethyl malonate in tetrahydrofuran was added under ice cooling, and the mixture was stirred at room temperature for 1 hour. To the mixture was added 1.74 g of 5-chrolo-3,4-dimethyl-2H-1,3-oxazine-2,6(3H)-dione, followed by stirring for 3.5 hours under heat refluxing condition. The reaction mixture was concentrated under reduced pressure. To the residue were sequentially added 20 ml of water and 15 ml of 1 mol/L hydrochloric acid, and the reaction was extracted with 85 ml of chloroform twice. The organic layer was dried with magnesium sulfate, filtered, and concentrated. The residue was washed with n-hexane to obtain 1.52 g of ethyl 5-chloro-1,6-dimethyl-4-hydroxy-2-oxo-1,2-dihydroropyridine-3-carboxylate represented by the formula:

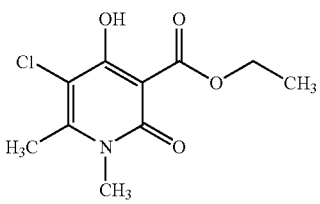

¹H-NMR (CDCl₃, TMS) δ (ppm): 1.45 (3H, t, J=7 Hz), 2.57 (3H, s), 3.54 (3H, s), 4.46 (2H, q, J=7 Hz), 14.10 (1H, s)

Reference Preparation Example 19

Using ethyl 2-fluoroacetoacetate in place of ethyl 2-chloroacetoacetate and according to the same manner as that of Reference Preparation Example 16, 5-fluoro-4-methyl-2H-1,3-oxazine-2,6(3H)-dione represented by the formula:

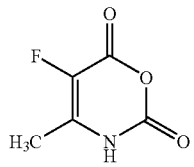

was obtained.

Reference Preparation Example 20

Using 5-fluoro-4-methyl-2H-1,3-oxazine-2,6(3H)-dione in place of 5-chloro-4-methyl-2H-1,3-oxazine-2,6(3H)-dione and according to the same manner as that of Reference Preparation Example 17, 5-fluoro-3,4-dimethyl-2H-1,3-oxazine-2,6(3H)-dione represented by the formula:

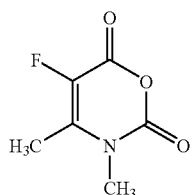

was obtained.

Reference Preparation Example 21

Using 5-fluoro-3,4-dimethyl-2H-1,3-oxazine-2,6(3H)-dione in place of 5-chloro-3,4-dimethyl-2H-1,3-oxazine-2,6(3H)-dione and according to the same manner as that of Reference Preparation Example 18, ethyl 5-fluoro-1,6-dimethyl-4-hydroxy-2-oxo-1,2-dihydropyridine-3-carboxylate represented by the formula:

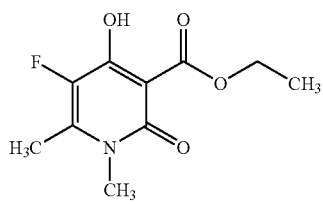

was obtained.

¹H-NMR (CDCl₃, TMS) δ (ppm): 1.45 (3H, d, J=7 Hz), 2.38 (3H, s), 3.46 (3H, s), 4.46 (2H, q, J=7 Hz), 13.67 (1H, s), 13.64 (1H, s)

Reference Preparation Example 22

14.4 g of a compound represented by the formula (XVII):

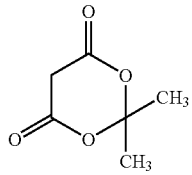

(XVII)

and 6.8 g of diketene were dissolved in 150 ml of acetonitrile, and 1.01 g of triethylamine was added thereto at room temperature. The mixture was stirred at room temperature for 1 hour. Then, 15.5 g of a 40% solution of methylamine in methanol was added to the mixture, followed by stirring at room temperature for 1 hour. Thereafter, the reaction mixture was cooled with an ice, and 30 ml of concentrated hydrochloric acid was added. The resulting crystals were collected by filtration and dried to obtain 17.6 g of 2,2-dimethyl-5-(1-hydroxy-3-methylamino-2-butenylidene)-1,3-dioxane-4,6-dione represented by the formula:

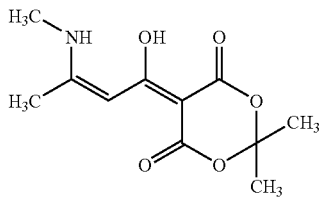

$^1$H-NMR (CDCl$_3$, TMS) δ (ppm): 1.70 (6H, s), 2.16 (3H, s), 3.09 (3H, d, J=4 Hz), 6.45 (1H, s), 8.82 (1H, br)

Reference Preparation Example 23

1.0 g of 2,2-dimethyl-5-(1-hydroxy-3-methylamino-2-butenylidene)-1,3-dioxane-4,6-dione was suspended in 20 ml of acetonitrile, 806 mg of N,N'-difluoro-2,2'-bipyridinium bis(tetrafluoroborate) was added thereto, and this was stirred at room temperature for 4 hours and at 50° C. for 30 minutes. The reaction mixture was added to 100 ml of ice water, and this was extracted with 100 ml of chloroform twice. The organic layer was dried with anhydrous magnesium sulfate and concentrated, and the residue was subjected to silica gel column chromatography (eluent: ethyl acetate) to obtain 480 mg of 5-fluoro-1,6-dimethyl-4-hydroxy-2-oxo-1,2-dihydropyridine-3-carboxylic acid represented by the formula:

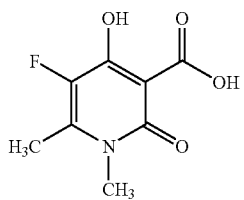

$^1$H-NMR (CDCl$_3$, TMS) δ (ppm): 2.47 (3H, s), 3.58 (3H, s), 13.89 (1H, br), 15.46 (1H, br)

Then, Formulation Examples will be shown. Part represents part by weight, and the present compound is indicated by a compound number described in Table 1 to Table 3.

Formulation Example 1

Fifty parts of each of the present compounds 1 to 26, 3 parts of calcium ligninsulfonate, 2 parts of sodium laurylsulfate, and 45 parts of synthetic hydrous silicon oxide are ground and mixed well to obtain each wettable powder.

Formulation Example 2

Twenty parts of each of the present compounds 1 to 26, and 1.5 parts of sorbitan trioleate are mixed with 28.5 parts of an aqueous solution containing 2 parts of polyvinyl alcohol, and finely-divided by a wet grinding method, 40 parts of an aqueous solution containing 0.05 part of xanthan gum and 0.1 part of aluminum magnesium silicate is added, 10 parts of propylene glycol is added and this is stirred and mixed to obtain each flowable preparation.

Formulation Example 3

Two parts of each of the present compounds 1 to 26, 88 parts of kaolin clay and 10 parts of talc are ground and mixed well to obtain each dust.

Formulation Example 4

Five parts of each of the present compounds 1 to 26, 14 parts of polyoxyethylene styryl phenyl ether, 6 parts of calcium dodecylbenzenesulfonate and 75 parts of xylene are mixed well to obtain each emulsifiable concentrate.

Formulation Example 5

Two parts of each of the present compounds 1 to 26, 1 part of synthetic hydrous silicon oxide, 2 parts of calcium ligninsulfonate, 30 parts of bentonite and 65 parts of kaolin clay are ground and mixed well, water is added, and the mixture is kneaded well, granulated and dried to obtain each granule.

Formulation Example 6

Ten parts of each of the present compounds 1 to 26, 35 parts of white carbon containing 50 parts of polyoxyethylene alkyl ether sulfate ammonium salt and 55 parts of water are mixed, and finely-divided by a wet grinding method to obtain each flowable preparation.

Then, Test Examples demonstrate that the present compound is useful as an agricultural and horticultural fungicide. The present compound is indicated by a compound number.

Test Example 1

Cucumber Grey Mold (*Botrytis cinerea*) Controlling Effect Test

Preventive Effect

A plastic pot was charged with a sand loam, and a cucumber (Name of plant variety: *Sagamihanpaku*) was seeded, and grown for 10 days in a greenhouse. Each of flowable preparations of the present compounds 1 to 5, 7, 11, 12, 16, 18 and 19 which had been obtained according to Formulation Example 6 was diluted with water to a predetermined concentration (500 ppm) to prepare a spraying solution. Each spraying solution was foliage-sprayed so that the solution was sufficiently adhered to cucumber leaves. After spraying, the cucumber was air-dried to such an extent that the spraying solution on the leaves was dried, and a PDA medium containing a spore of cucumber grey mold (*Botrytis cinerea*) was placed on the cucumber leaves. After inoculation, the cucumber was placed under high humidity at 12° C. for 5 days, and the controlling effect was investigated. As a result, an area of a lesion in a plant treated with the present compound 1 to 5, 7, 11, 12, 16, 18 or 19 was 10% or less an area of a lesion in a non-treated plant.

Test Example 2

Wheat Scab (*Fusarium culmorum*) Controlling Effect Test (Preventive Effect)

A plastic pot was charged with a sand loam, and a wheat (Name of plant variety: *shirogane komugi*) was seeded, and was grown for 8 days in a greenhouse. Each of flowable preparations of the present compounds 4, 6, 8, 11 and 14 which had been obtained according to Formulation Example 6 was diluted with water to a predetermined concentration (500 ppm) to prepare a spraying solution. Each spraying solution was foliage-sprayed so that the solution was sufficiently adhered to wheat leaves. After spraying, the wheat was air-dried to such an extent that the spraying solution on the leaves was dried, and a spore suspension of wheat scab (*Fusarium culmorum*) (containing about 2000000 spores per 1 ml of suspension) was spraying-inoculated (ratio of about 2 ml per one plant). After spraying, the wheat was placed under high humidity at 23° C. for 4 days, and was further placed in a greenhouse 23° C. for 3 days.

Thereafter, the controlling effect was investigated. As a result, an area of a lesion in a plant treated with the present compound 4, 6, 8, 11 or 14 was 10% or less an area of a lesion in a non-treated plant.

Industrial Applicability

By using the present compound, plant diseases can be controlled.

The invention claimed is:
1. A carboxamide compound represented by the formula (I):

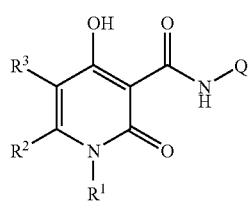

wherein Q represents a nitrogen-containing 6-membered aromatic heterocyclic group optionally fused with a benzene ring, two or more of ring constitutional atoms of the heterocyclic group are nitrogen atoms, the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group, $R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end to represent a C3-C4 alkylene group, and $R^3$ represents a hydrogen atom, a halogen atom or a C1-C3 alkyl group.

2. The carboxamide compound according to claim 1, wherein Q represents a nitrogen-containing 6-membered aromatic heterocyclic group optionally fused with a benzene ring, two or more of ring constitutional atoms of the heterocyclic group are nitrogen atoms, the heterocyclic group may be substituted with at least one group selected from the group consisting of a C1-C3 alkyl group, a C1-C3 haloalkyl group, a C1-C3 alkoxy group, a halogen atom, a cyano group and a nitro group, $R^1$ represents a C1-C3 alkyl group or a C2-C5 alkoxyalkyl group, $R^2$ represents a hydrogen atom or a C1-C3 alkyl group, or $R^1$ and $R^2$ are bound to each other at an end to represent a C3-C4 alkylene group, and $R^3$ represents a hydrogen atom, a halogen atom or a C1-C3 alkyl group.

3. The carboxamide compound according to claim 1, wherein Q is a 6-membered aromatic heterocyclic group in which two or more ring constitutional atoms are nitrogen atoms, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group.

4. The carboxamide compound according to claim 1, wherein Q is a 6-membered aromatic heterocyclic group in which two or more ring constitutional atoms are nitrogen atoms, and the heterocyclic group may be substituted with at least one group selected from the group consisting of a C1-C3 alkyl group, a C1-C3 haloalkyl group, a C1-C3 alkoxy group, a halogen atom, a cyano group and a nitro group.

5. The carboxamide compound according to claim 1, wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group, a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl) C1-C3 alkylthio group, a halogen atom, a cyano group and a nitro group.

6. The carboxamide compound according to claim 1, wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group; a 1,3,5-triazin-2-yl group, a quinoxalin-2-yl group, a quinazolin-2-yl group or a cinnolin-3-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group.

7. The carboxamide compound according to claim 1, wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a C1-C3 alkylthio group, a (C1-C3 alkoxycarbonyl)C1-C3 alkylthio group, a halogen atom, a cyano group and a nitro group.

8. The carboxamide compound according to claim 1, wherein Q is a heterocyclic group which is a 2-pyrimidinyl group, a 4-pyrimidinyl group, a 5-pyrimidinyl group, a 2-pyrazinyl group, a 3-pyridazinyl group, a 4-pyridazinyl group, a 1,2,4-triazin-3-yl group or a 1,3,5-triazin-2-yl group, and the heterocyclic group may be substituted with at least one group selected from the group consisting of a C1-C3 alkyl group, a C1-C3 haloalkyl group, a C1-C3 alkoxy group, a halogen atom, a cyano group and a nitro group.

9. The carboxamide compound according to claim 1, wherein $R^3$ is a hydrogen atom or a C1-C3 alkyl group.

10. The carboxamide compound according to claim 1, wherein $R^3$ is a hydrogen atom or a halogen atom.

11. A plant disease controlling agent, comprising a carboxamide compound as defined in claim 1 as an active ingredient, and an inert carrier.

12. A method of controlling a plant disease, comprising a step of treating a plant or a soil where a plant grows with an effective amount of the carboxamide compound as defined in claim 1.

\* \* \* \* \*